US007998732B2

(12) United States Patent
Chartrain et al.

(10) Patent No.: US 7,998,732 B2
(45) Date of Patent: Aug. 16, 2011

(54) PROCESS FOR LARGE SCALE PRODUCTION OF PLASMID DNA BY E. COLI FERMENTATION

(75) Inventors: Michel Chartrain, Westfield, NJ (US); Laura Kizer Bentley, Monmouth, NJ (US); Barbara Ann Krulewicz, Bloomfield, NJ (US); Kristin M. Listner, East Windsor, NJ (US); Wen-jun Sun, Edison, NJ (US); Chanyong Brian Lee, Thousand Oaks, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 763 days.

(21) Appl. No.: 10/588,295

(22) PCT Filed: Jan. 31, 2005

(86) PCT No.: PCT/US2005/002911
§ 371 (c)(1),
(2), (4) Date: Aug. 4, 2006

(87) PCT Pub. No.: WO2005/078115
PCT Pub. Date: Aug. 25, 2005

(65) Prior Publication Data
US 2008/0274452 A1 Nov. 6, 2008

Related U.S. Application Data

(60) Provisional application No. 60/541,894, filed on Feb. 4, 2004.

(51) Int. Cl.
C12N 15/63 (2006.01)
C12N 1/21 (2006.01)
C12N 15/70 (2006.01)
(52) U.S. Cl. .................. 435/320.1; 435/252.3; 435/471
(58) Field of Classification Search .................. None
See application file for complete search history.

(56) References Cited

U.S. PATENT DOCUMENTS

| | | | |
|---|---|---|---|
| 4,604,234 A | 8/1986 | Fugii et al. | |
| 5,015,573 A | 5/1991 | Yarranton et al. | |
| 5,639,658 A | 6/1997 | Drobish et al. | |
| 5,914,390 A | 6/1999 | Nathan et al. | |
| 6,503,738 B1 | 1/2003 | Thatcher et al. | |

FOREIGN PATENT DOCUMENTS

| | | |
|---|---|---|
| WO | WO 82/02901 | 9/1982 |
| WO | WO 96/40905 | 12/1996 |
| WO | WO 98/37179 | 8/1998 |

OTHER PUBLICATIONS

Website microbelibrary.org. www.microbelibrary.org/asmonly/details.asp?id=2038. 2009.*
Kongo et al Food Microbio. and Safety 68(9): 2742-2476, 2003.*
Voziyanov et al Nuc. Acid Res. 30(7): 1656-1663, 2002.*
Chen, W., et al., Journal of Industrial Microbiology & Biotechnology, "Automated fed-batch fermentation with feed-back controls based on dissolved oxygen (DO) and pH for production of DNA vaccines", vol. 18, pp. 43-48, 1997.
Ely, Susan, et al., Mol. Gen Genet, "Regulation of plasmid DNA synthesis: Isolation and characterization of copy number mutants of miniR6-5 and miniF plasmids", vol. 181, pp. 29-35, 1981.
Korz, D.J., et al., Journal of Biotechnology, "Simple fed-batch technique for high cell density cultivation of *Escherichia coli*", vol. 39, pp. 59-65, 1995.
Lahijani, et al., Human Gene Therapy, "High-yield production of pBR322-derived plasmids intended for human gene therapy by employing a temperature-controllable point mutation", vol. 7, pp. 1971-1980, 1996.
Lee, Sang Yup, Tibtech, "High cell-density culture of *Escherichia coli*", vol. 14, pp. 98-105, 1996.
Prather, Kristala Jones, et al., Enzyme and Microbial Technology, "Industrial scale production of plasmid DNA for vaccine and gene therapy: plasmid design, production, and purification", vol. 33, pp. 865-883, 2003.
Namdev, Pradyumna K., et al., Biotechnology and Bioengineering, "Effect of oxygen fluctuations on Recombinant *Escherichia coli* Fermentation", vol. 41, pp. 666-670, 1993.
O'Kennedy, R.D., et al., Journal of Biotechnology, "Effects of growth medium selection on plasmid DNA production and initial processing steps", vol. 76, pp. 175-183, 2000.
O'Kennedy, et al., Biotechnol. Appl. Biochem. "Effects of fermentation strategy on the characteristics of plasmid DNA production", vol. 37, pp. 83-90, 2003.
Prazeres, Duarte M. F., et al., Tibtech, "Large-scale production of pharmaceutical-grade plasmid DNA for gene therapy: problems and bottlenecks", vol. 17, pp. 169-174, 1999.
Reinikainen, P., et al., Biotechnology Letters, "*Escherichia coli* growth and plasmid copy numbers in continuous cultivations", vol. 11, No. 4, pp. 225-230, 1989.

(Continued)

*Primary Examiner* — Michele Joike
(74) *Attorney, Agent, or Firm* — Melissa B. Wenk; Sheldon O. Heber

(57) ABSTRACT

The present invention relates generally to a method for increasing the yield of plasmid DNA production. The method includes the steps of selecting a highly productive clonal subtype of a strain of *E. coli*, including but not limited to the DH5 strain, harboring a DNA plasmid and cultivating said clonal subtype with fed-batch fermentation in a chemically-defined medium. The plasmid DNA production process described herein can generate record quantities of plasmid DNA when said highly productive clonal subtypes are cultivated on an industrial scale. The disclosed method can be used for the production of pharmaceutical grade DNA for use in polynucleotide vaccination and gene therapy treatment regimens.

13 Claims, 12 Drawing Sheets

OTHER PUBLICATIONS

Reinikainen, P., et al., Biotechnology and Bioengineering, "*Escherichia coli* plasmid production in fermenter", vol. 33, pp. 386-393, 1989.

Riesenberg, D., et al., Journal of Biotechnology, "High cell density cultivation of *Escherichia coli* at controlled specific growth rate", vol. 20, pp. 17-28, 1991.

Riesenberg, D. et al., Current Opinion in Biotechology, "High-cell-density cultivation of *Escherichia coli*", vol. 2, No. 3, pp. 380-384, 1991.

Seo, Jin-Ho, et al., Biotechnology and Bioengineering, "Continuous cultivation of recombinant *Escherichia coli*: existence of an optimum dilution rate for maximum plasmid and gene product concentration", vol. XXVIII, pp. 1590-1594, 1986.

Wang, Zhijun, et al., Process Biochemistry, "Medium design for plasmid DNA production based on stoichiometric model", vol. 36, pp. 1085-1093, 2001.

Yee, L., et al., Biotechnology, "Recombinant protein expression in high cell density fed-batch cultures of *Escherichia coli*", vol. 10, pp. 1150-1556, 1992.

Zhang, J., et al., Appl. Microbiol. Biotechnology, "Chemically defined media for commercial fermentations", vol. 51, pp. 407-421, 1999.

Cress, D. et al. "Isolation and Characterization of *Escherichia coli* Chromosomal Mutants Affecting Plasmid Copy Number", Journal of Bacteriology, 1976, vol. 125, pp. 635-642.

Mason, C. et al. "Effects of plasmid presence on growth and enzyme activitiy of *Escherichia coli* DH5α", Appl. Microbiol. Biotechnol., 1989, vol. 32, pp. 54-60.

Metcalf, W. et al. "Use of the *rep* technique for allele replacement to construct new *Escherichia coli* hosts for maintenance of R6Kγ origin plasmids at different copy numbers", Gene, 1994, vol. 138, pp. 1-7.

Seo, J. et al. "Effects of Recombinant Plasmid Content on Growth Properties and Cloned Gene Product Formation in *Escherichia coli*", Biotechnology and Bioengineering, 1985, vol. 27, pp. 1668-1674.

* cited by examiner

FIG. 1

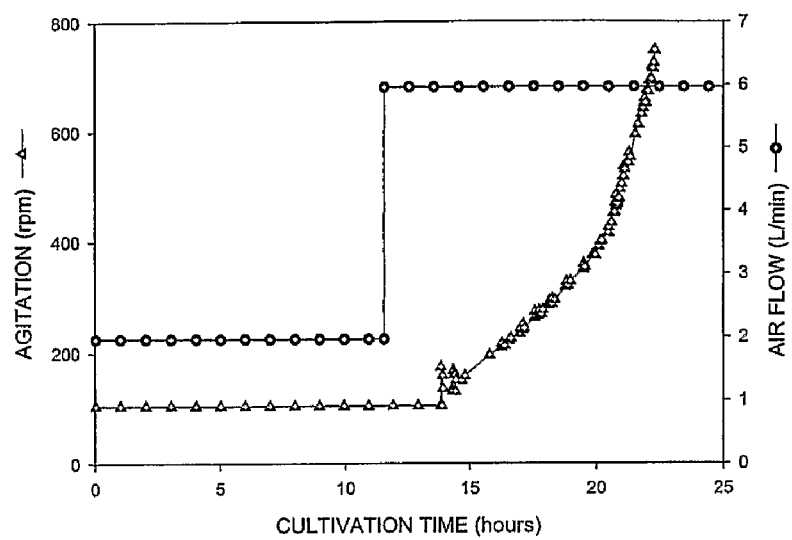
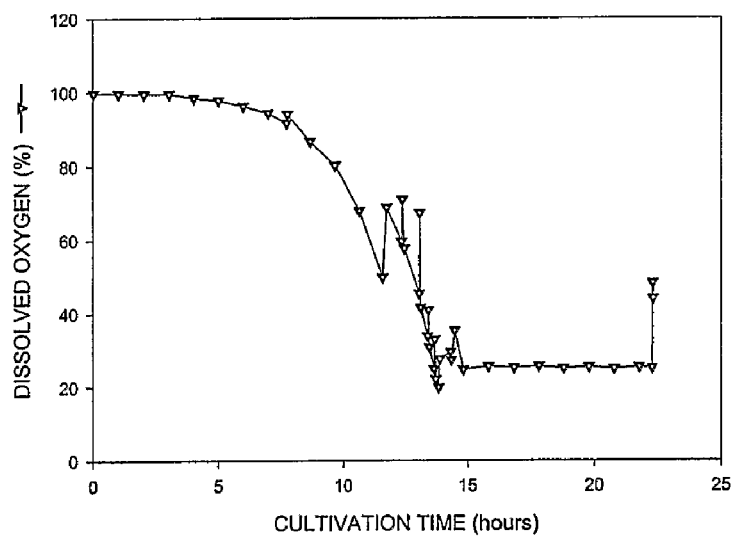
FIG. 3A-B

A.
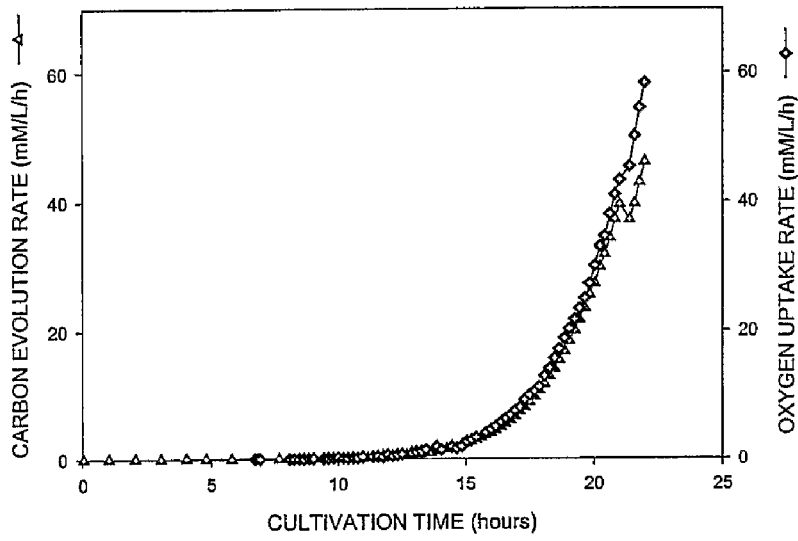
B.
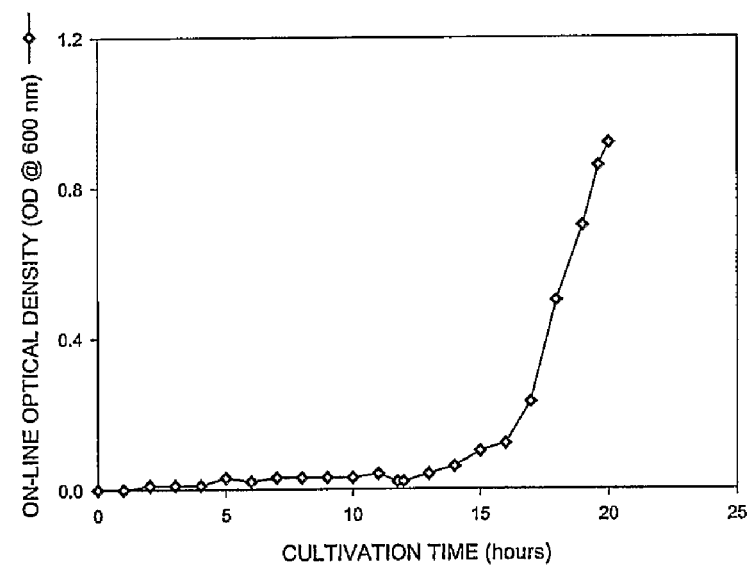
FIG. 4A-B

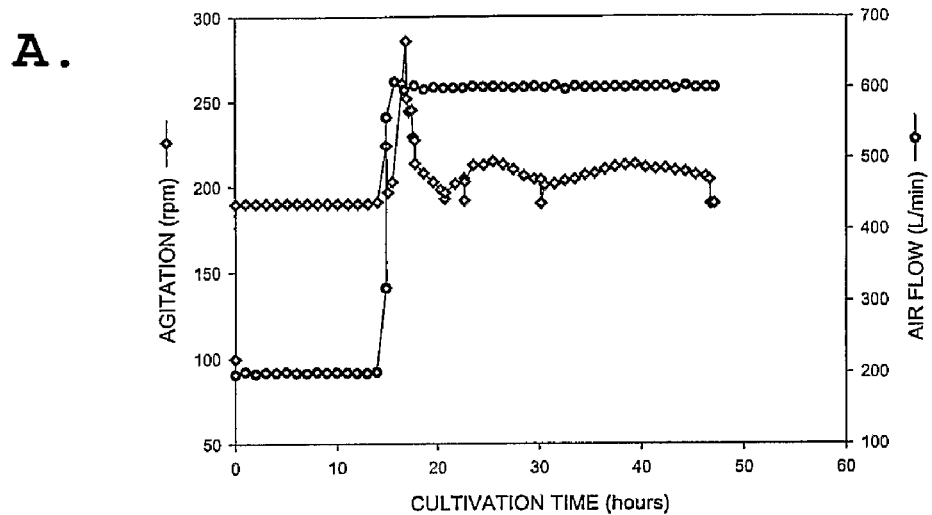
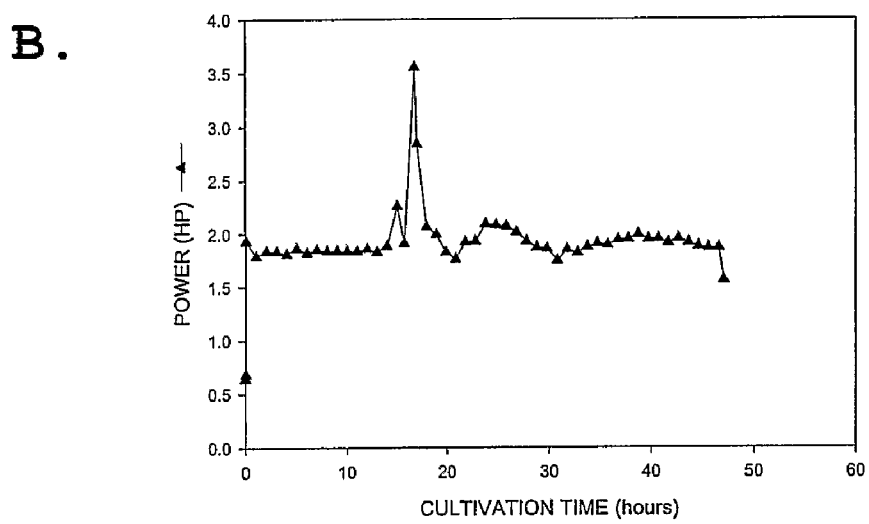
FIG. 6A-B

A.
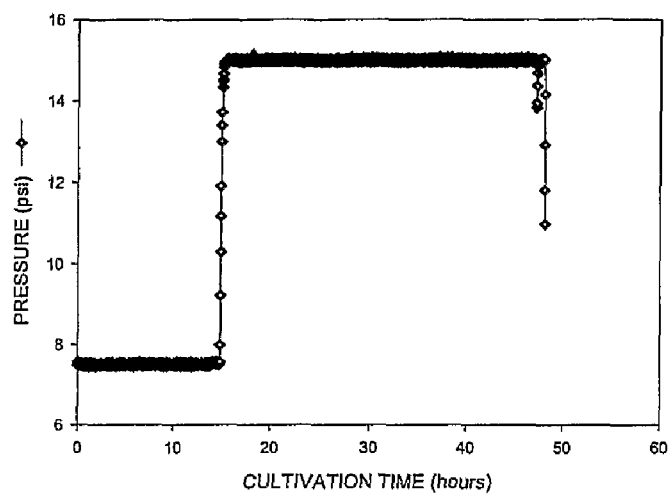
B.
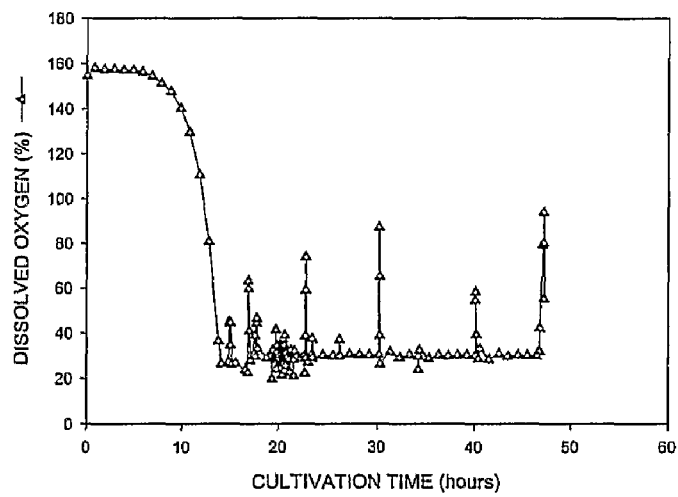
FIG. 7A-B

A.
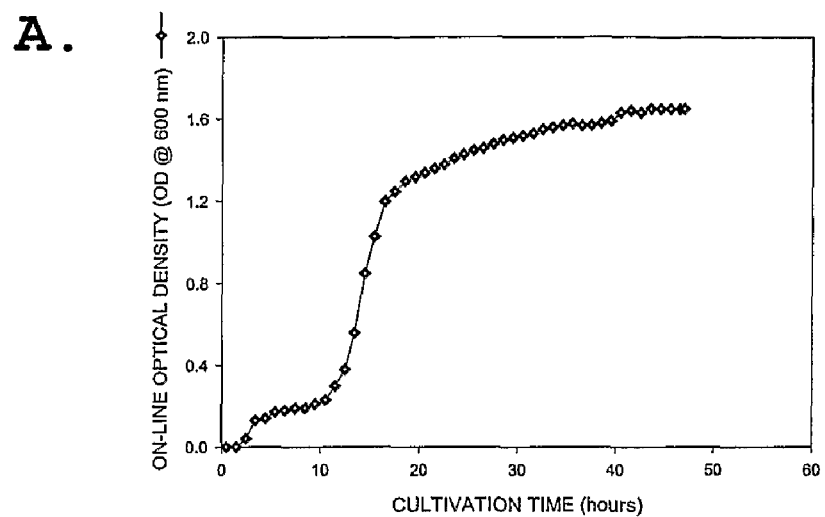
B.
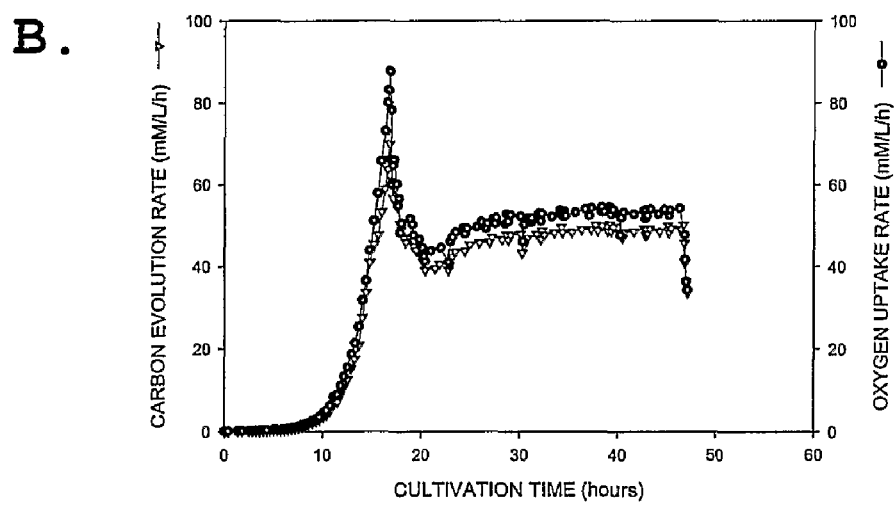
FIG. 8A-B

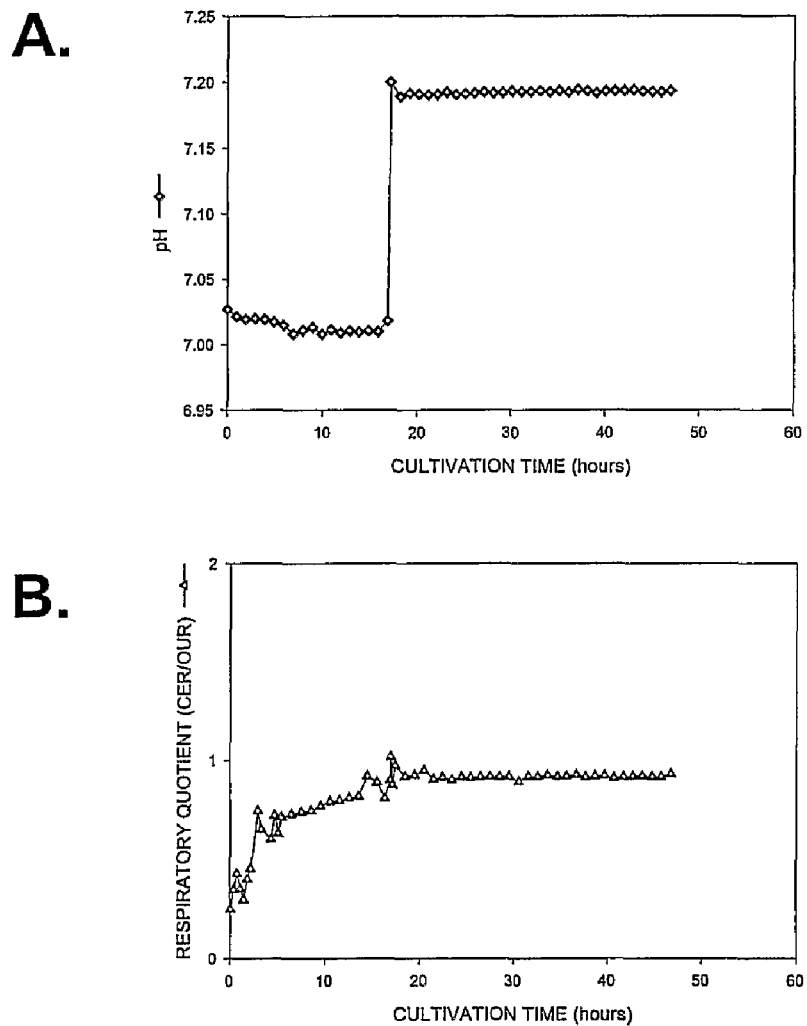
FIG. 9A-B

A.
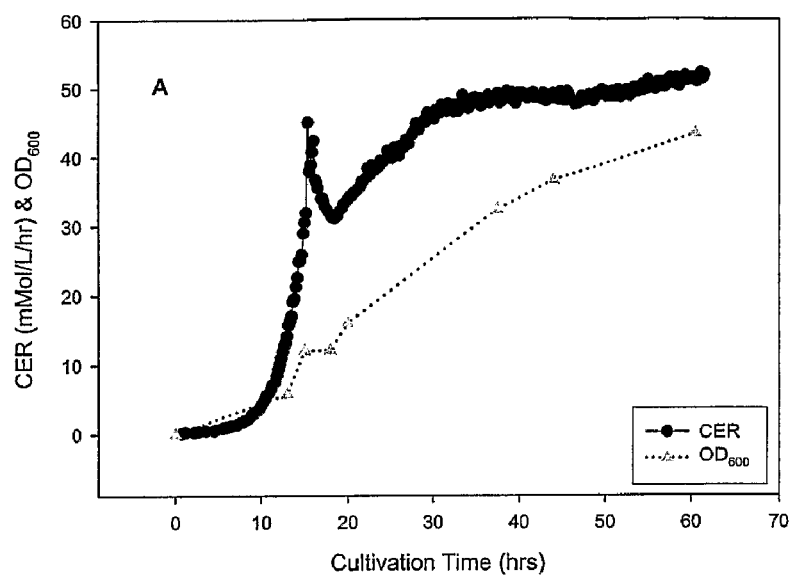
Yields
B.
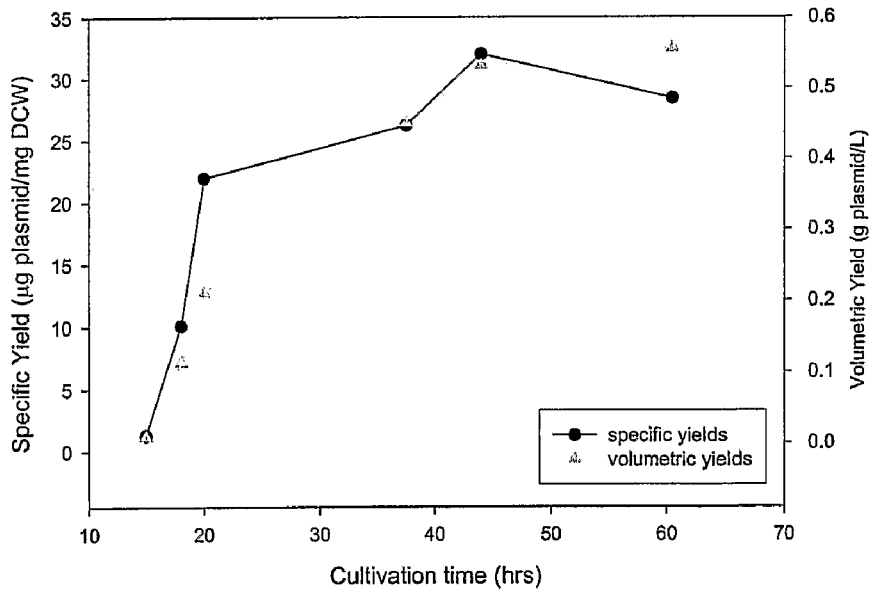
FIG.10A-B

A.
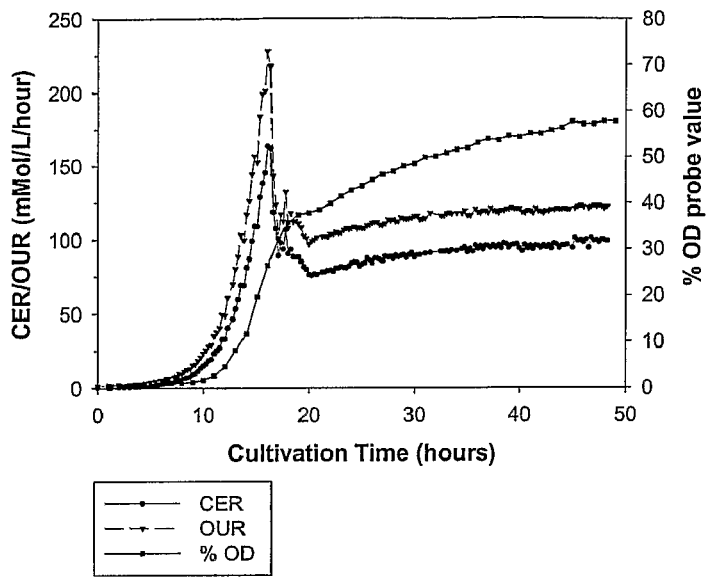
B.
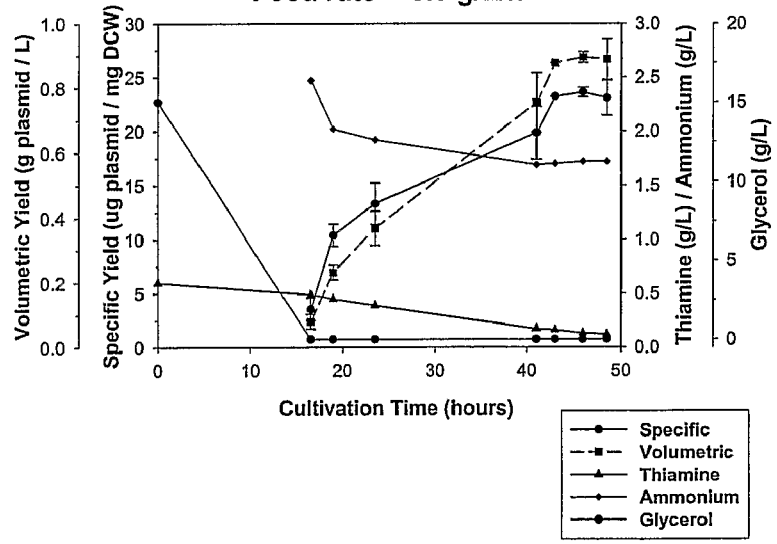
FIG. 11A-B

A.
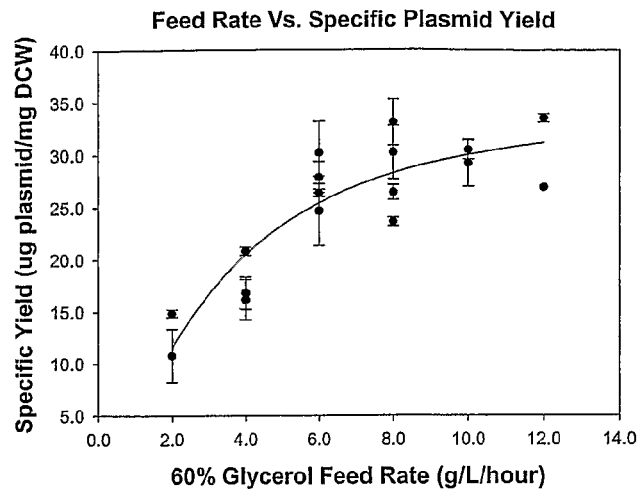
B.
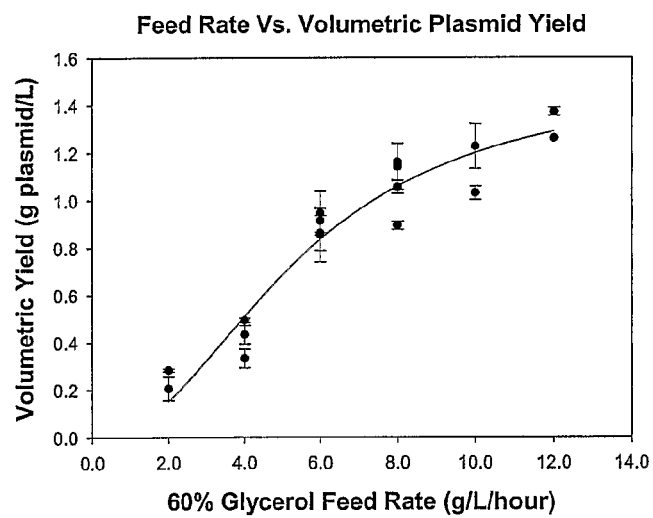
FIG. 12A-B

PROCESS FOR LARGE SCALE PRODUCTION OF PLASMID DNA BY *E. COLI* FERMENTATION

CROSS-REFERENCE TO RELATED APPLICATIONS

The present application is the national stage entry of PCT International Application No. PCT/US2005/002911, having an international filing date of Jan. 31, 2005, which claims the benefit of priority to U.S. Provisional Application No. 60/541,894, filed Feb. 4, 2004, hereby incorporated by reference herein.

FIELD OF THE INVENTION

The present invention relates to a process for the production of plasmid DNA comprising the steps of: (a) selecting a highly productive clonal subtype of a strain of *E. coli* harboring a DNA plasmid, wherein a highly productive clonal subtype exhibits a higher plasmid copy number per cell in comparison to non-selected, transformed *E. coli* clonal subtypes of the same strain; and, (b) cultivating said highly productive clonal subtype with fed-batch fermentation in chemically-defined medium. In one embodiment of the present invention, the plasmid DNA production process described herein generates large quantities of plasmid DNA as a result of cultivating said highly productive clonal subtypes on an industrial scale. The present invention further relates to methods for selecting highly productive clonal subtypes of a strain of *E. coli*, including but not limited to highly productive clones of DH5 cells, for the production of plasmid DNA. The process and methods disclosed herein can be used to generate pharmaceutical grade plasmid DNA for polynucleotide vaccination and gene therapy treatment regimens.

BACKGROUND OF THE INVENTION

DNA vaccines are an innovative approach for inducing protective immunity against specific diseases encompassing the targeted delivery of plasmid DNA to cells (Montgomery, D. L. et al., 1993, *Cell Biol.* 169:244-247; Ulmer, J. B. et al., 1993, *Science* 259:1745-1749). DNA vaccines are capable of producing neutralizing antibodies, as well as inducing the more preferable cell-mediated immune ("CMI") responses. Typically, DNA vaccines are generated by first inserting into a plasmid a gene encoding an antigen of interest, said plasmid containing a promoter active in mammalian cells. The plasmid is then transformed into a recombinant microbial host such as *Escherichia coli* ("*E. coli*") where it is amplified and then purified. The plasmid DNA, normally suspended in saline, is administered to the body by either injection directly into muscle cells or by particle bombardment. The plasmid DNA internalized by the muscle cells is transcribed and translated, and the expressed protein is transported to the cell's surface for T-cell presentation. This mode of action results in subsequent humoral and CMI responses against the expressed antigen. Importantly, the administered plasmid DNA is non-infectious, does not replicate, and only encodes the protein of interest. Preclinical immunogenicity and efficacy of DNA vaccines in disease models have been demonstrated for a number of infectious diseases including cancer, allergy and autoimmune diseases (for review, see Gurunathan, S. et al., *Ann. Rev. Immunol.* 2000; 18:927-974). Clinical trials assessing the ability of DNA vaccines to generate protective immune responses against HIV, malaria, influenza, hepatitis B and cancer have been reported (for review, see Gurunathan, S. et al., 2000, *Curr. Opin. Immunol.* 12:442-447; Shroff, K. et al., 1999, *PSTT* 2:205-212; and Restifo, N. & S. Rosenberg, 1999, *Curr. Opin. Oncol.* 11:50-57). Recently, mixed modality vaccines have demonstrated a promising strategy whereby DNA vaccines are combined with other gene-delivery systems. Preclinical data has shown that administering plasmid DNA as a prime, followed by another gene-based vector system encoding the same antigen as a boost, results in greater immune responses than if either vector is used for both the prime and boost.

Plasmid DNA has additionally been approved for gene therapy treatment. Gene therapy encompasses the administration of a functional gene into the body, delivery of said gene to the target cell, and expression of the therapeutic product with the intent to selectively correct or modulate disease conditions. Gene therapy represents an alternative for the prevention, treatment or cure of genetic defects. Many plasmid DNA-based gene therapy clinical trials have been initiated (for review, see Mountain, A., 2000, *TIBTECH* 18:119-128; and Ferber, D., 2001, *Science* 294:1638-1642).

For use in both polynucleotide vaccination and gene therapy regimes, genes in the form of DNA plasmids can be formulated like conventional pharmaceutical products and administered directly to patients. The potential number of human users for DNA vaccines or gene therapy to combat disease, either as part of a prophylactic or therapeutic regimen, is very high, creating a large demand for plasmid DNA. DNA vaccines for veterinary diseases will likely further increase this demand. Additionally, milligram quantities of plasmid DNA may be needed for effective treatment since it has been shown that only a small number of plasmid molecules presented to a cell reach the nucleus where the gene of interest is expressed (Leitner, W. et al., 2000, *Vaccine* 18:765-777). Thus, the manufacture and purification of large quantities of pharmaceutical-grade DNA is crucial.

High yield plasmid DNA production processes are necessary to fully develop and exploit the advantages that both DNA vaccine and gene therapy treatment options have to offer. For these reasons, there is a continued need to increase the productivity of plasmid DNA manufacturing and purification methodologies. Many described methods for increasing plasmid DNA production for use in gene therapy or polynucleotide vaccination focus on the plasmid purification step, i.e. the downstream part of the production process; however, much less is known about how to optimize the initial fermentation step of the production process for the generation of plasmid DNA, especially for production at an industrial scale. Despite prior investigations into small scale plasmid DNA purification methodologies, it has been difficult to scale up the manufacture and purification of clinical-grade plasmid DNA (Prazeres, D. M. F. et al., 1999, *TIBTECH* 17:169-174). Using non-optimized laboratory conditions for the production of plasmid DNA invariably leads to very low (5-40 mg/L) volumetric yields. Increasing the productivity of plasmid DNA manufacturing processes requires the concomitant optimization of plasmid copy number (i.e., specific yield) and biomass concentration (i.e., volumetric yield). While some techniques identified for optimizing fermentation methods for recombinant protein production by *E. coli* on a commercial scale may be translatable to processes aimed at the overproduction of plasmid, the conditions facilitating optimal protein expression will likely differ to some degree from those necessary for achieving high plasmid copy number.

PCT International Application PCT/US96/09746 (International publication number WO 96/40905) discloses a fed-batch fermentation method for generating production scale quantities of pharmaceutical grade plasmid DNA in a microorganism at high efficiencies whereby growth rate is limited to achieve optimum yield.

PCT International Application PCT/EP98/01122 (International publication number WO 98/37179) discloses the use of chemically-defined medium for the fermentative production of valuable compounds on an industrial scale, in addition to the selection of a high growth strain on said chemically-defined medium after mutagenic treatment.

U.S. Pat. Nos. 5,981,735 and 6,503,738, issued to Thatcher et al. on Nov. 9, 1999 and Jan. 7, 2003, respectively, disclose a scalable method for the production of highly purified plasmid DNA in E. coli consisting of growing plasmid-containing cells to a high biomass in exponential growth and lysing the cells by raising the pH of the culture to a value in which chromosomal DNA is denatured but plasmid DNA is reversibly renatured.

O'Kennedy, R. et al. (2000, J. Biotechnol. 76:175-183) show that culturing E. coli DH5α cells harboring the plasmid pSVβ in a semi-defined medium results in higher plasmid specific yields over the standard complex Luria Bertrani ("LB") medium formulation, demonstrating the existence of an optimum carbon/nitrogen ratio.

The present invention discloses a highly productive, scalable and reproducible process for the production of plasmid DNA. The process combines the selection of highly productive clones of E. coli with the induction of plasmid amplification during fermentation as a result of utilizing a limited nutrient feeding regime in a chemically-defined medium. This process is useful for the production of plasmid DNA for gene therapy and genetic vaccination for a number of human and animal diseases, including HIV, hepatitis C and rabies.

SUMMARY OF THE INVENTION

The present invention discloses a process for the production of plasmid DNA, comprising the steps of: (a) selecting a highly productive clonal subtype of a strain of E. coli harboring a DNA plasmid; and, (b) cultivating said highly productive clonal subtype with fed-batch fermentation in chemically-defined medium. According to the present invention, highly productive clonal subtypes of a strain of E. coli, including but not limited to DH5 cells, harboring a DNA plasmid exhibit a higher plasmid copy number per cell in comparison to non-selected, transformed E. coli clonal subtypes of the same strain that are similarly tested. In one embodiment of the present invention, the plasmid DNA production process described herein generates record quantities of plasmid DNA as a result of cultivating said highly productive clonal subtypes on an industrial scale. Thus, the DNA production process of the present invention can result in an increase in yield of plasmid DNA when compared to other large-scale, plasmid DNA production processes.

The present invention further relates to a plasmid DNA production process as described above wherein said selection component comprises a two-step process: a first selection step wherein potential highly productive clonal subtypes of a strain of E. coli, including but not limited to the DH5 strain, are isolated; followed by a second selection step wherein said potential highly productive clonal subtypes previously isolated are tested in a small-scale fermentation system to determine which clonal subtypes are highly productive. In one embodiment of the present invention, said potential highly productive clonal subtypes are selected on a chemically-defined medium.

In one embodiment of the present invention, colonies of potential highly productive clonal subtypes of E. coli selected by methods disclosed herein are phenotypically gray when plated on blood agar as an indicator. In another embodiment of the present invention, colonies of potential highly productive clonal subtypes of E. coli are phenotypically cream when plated on chemically-defined agar medium and incubated until a population of both cream-colored colonies and cream-colored colonies with brown, bulls-eyed centers has formed.

In a further embodiment of the present invention, the productivity (i.e., plasmid copy number per cell) of said potential highly productive clonal subtypes of E. coli, including but not limited to DH5 cells, selected in step one of the selection process of the present invention is determined after cultivating said clonal subtypes in a small-scale fermentation system. In one embodiment of the present invention, this small-scale fermentation system consists of shake flask fermentation with a nutrient feeding regime. The shake flask fermentation system simulates the fermentation regime used in the ultimate production protocol to generate the desired plasmid DNA. In another embodiment of the present invention, the clonal subtypes evaluated using a small-scale fermentation system, including but not limited to a shake flask fermentation system, are cultivated in a chemically-defined medium. In a further embodiment, a carbon and/or nitrogen solution is continuously fed to said small-scale fermentation system when said clonal subtypes are in mid-logarithmic phase of growth.

The present invention relates to a process for the production of plasmid DNA comprising cultivating highly productive E. coli clonal subtypes, including but not limited to highly productive clonal subtypes of DH5 cells, harboring a DNA plasmid using fed-batch technology. In one embodiment of the present invention, selection of potential highly productive E. coli clonal subtypes, as described herein, occurs on chemically-defined medium. Both the subsequent evaluation of said potential highly productive E. coli clonal subtypes to determine which clones exhibit a higher than normal specific productivity, and the final fermentation regime, occurs in chemically-defined medium. In one embodiment of the invention, the highly productive clonal subtypes identified as described herein are selected and/or cultivated in a chemically-defined medium selected from the group consisting of DM-P5, DME-B12, Medium C, Medium D, Medium E, Medium F and Medium G.

The present invention further relates to a fermentation process, including but not limited to a large-scale fermentation process, for the production of plasmid DNA, as described herein, whereby the cultivation regime of the process comprises at least one production stage fermentation phase. In a further embodiment of the invention, a carbon and/or nitrogen solution is fed to a production stage fermentor when the selected, highly productive clonal subtype of E. coli harboring a DNA plasmid is in mid-logarithmic phase of growth. In another embodiment of the present invention, the feed solution comprises about 50% glycerol (v/v) and about 25% monosodium glutamate (w/v). In a further embodiment, the feed solution comprises about 60% glycerol (v/v).

The present invention relates to methods for selecting a highly productive clonal subtype of E. coli, including but not limited to DH5 cells, for the production of plasmid DNA. In one embodiment of the present invention, said highly productive clonal subtypes of a strain of E. coli are selected via a method comprising the steps of: (a) purifying colonies of a strain of E. coli harboring a DNA plasmid that are phenotypically gray when plated on blood agar as an indicator, wherein a gray-colored colony represents a potential highly productive clonal subtype; and, (b) testing productivity of said potential highly productive clonal subtypes, wherein a highly productive clonal subtype exhibits a higher plasmid copy number per cell in comparison to non-selected, transformed E. coli clonal subtypes of the same strain tested under similar fermentation conditions. In another embodiment of the present invention, a highly productive clonal subtype of E. coli cells is selected via a method comprising the steps of: (a) incubating a strain of E. coli harboring a DNA plasmid plated on chemically-defined agar medium until a population of both cream-colored colonies and cream-colored colonies with brown, bulls-eye centers have formed; (b) purifying said cream-colored colonies from step (a), wherein a cream-colored colony represents a potential highly productive clonal subtype; and, (c) testing productivity of said potential highly productive clonal subtypes of step (b), wherein a highly productive clonal subtype exhibits a higher plasmid copy number per cell in comparison to non-selected, transformed E. coli clonal subtypes of the same strain tested under similar fermentation conditions.

BRIEF DESCRIPTION OF THE DRAWINGS

FIG. 1 shows the percentage of gray-colored colonies identified by the blood agar phenotype screening assay present in cultures of a DNA vaccine candidate, Influenza M1. The percentage of gray colonies produced when plated on blood agar increased from 44% to 89% over the course of four enrichments, demonstrating the selective growth advantage of clonal isolates purified from gray phenotypic colonies over those purified from white-colored colonies.

FIG. 3 summarizes key data gathered for a typical seed fermentor including airflow rate (panel A), agitation speed (panel A) and percent dissolved oxygen (panel B). This data was generated from a seed fermentor used to cultivate cells containing the V1Jns-gag plasmid according to Plasmid Production Method 1 of Example 9.

FIG. 4 summarizes more key data gathered for a typical seed fermentor, as demonstrated by a seed fermentor used to cultivate cells containing the V1Jns-gag plasmid according to Plasmid Production Method 1 of Example 9. The data includes oxygen uptake rate (panel A), carbon evolution rate (A) and optical density (panel B).

FIG. 6 summarizes the key data collected for a typical production fermentor including airflow rate (panel A), agitation speed (panel A) and power (panel B). This data was generated from a production fermentor used to cultivate cells containing the V1Jns-gag plasmid according to Plasmid Production Method 1 of Example 9.

FIG. 7 summarizes more key data gathered for a typical production fermentor, as demonstrated by a production fermentor used to cultivate cells containing the V1Jns-gag plasmid according to Plasmid Production Method 1 of Example 9. The data includes pressure (panel A) and percent dissolved oxygen (panel B).

FIG. 8 summarizes key optical density (panel A), carbon dioxide evolution rate (panel B) and oxygen uptake rate (panel B) data gathered for a typical production fermentor, as demonstrated by a production fermentor used to cultivate cells containing the V1Jns-gag plasmid according to Plasmid Production Method 1 of Example 9.

FIG. 9 summarizes key pH (panel A) and respiratory quotient (panel B) data gathered for a typical production fermentor, as demonstrated by a production fermentor used to cultivate cells containing the V1Jns-gag plasmid according to Plasmid Production Method 1 of Example 9.

FIG. 10 presents the carbon dioxide evolution rate ("CER") (panel A), growth ($OD_{600}$) (panel A) and plasmid production profiles (panel B) from the production fermentor used to cultivate cells containing the V1Jns-gag plasmid according to Plasmid Production Method 2 of Example 9.

FIG. 11 presents the results obtained from the cultivation of cells containing the V1Jns-gag plasmid according to Plasmid Production Method 3 of Example 9. Panel A shows the carbon dioxide evolution rate, oxygen uptake rate ("OUR") and on-line optical density ("OD") measurements. The cells were cultivated in a production fermentor and fed with 50% glycerol (v/v) and 25% MSG (w/v) at a rate of 2.66 to 3.66 g/L/h. Panel B shows the volumetric (g plasmid/L) and specific yields (μg plasmid/mg dry cell weight), as well as thiamine, ammonium, and glycerol concentrations over the course of fermentation.

FIG. 12 presents the results obtained from the cultivation of cells containing the V1Jns-gag plasmid according to Plasmid Production Method 3 of Example 9 wherein the production fermentor was fed with 60% (v/v) glycerol at rates between 2.0 and 12 g/L/h. Panel A compares the specific yields (μg plasmid/mg dry cell weight) produced from each fermentation regime, while panel B compares the volumetric yields (g plasmid/L).

DETAILED DESCRIPTION OF THE INVENTION

Figure 2:
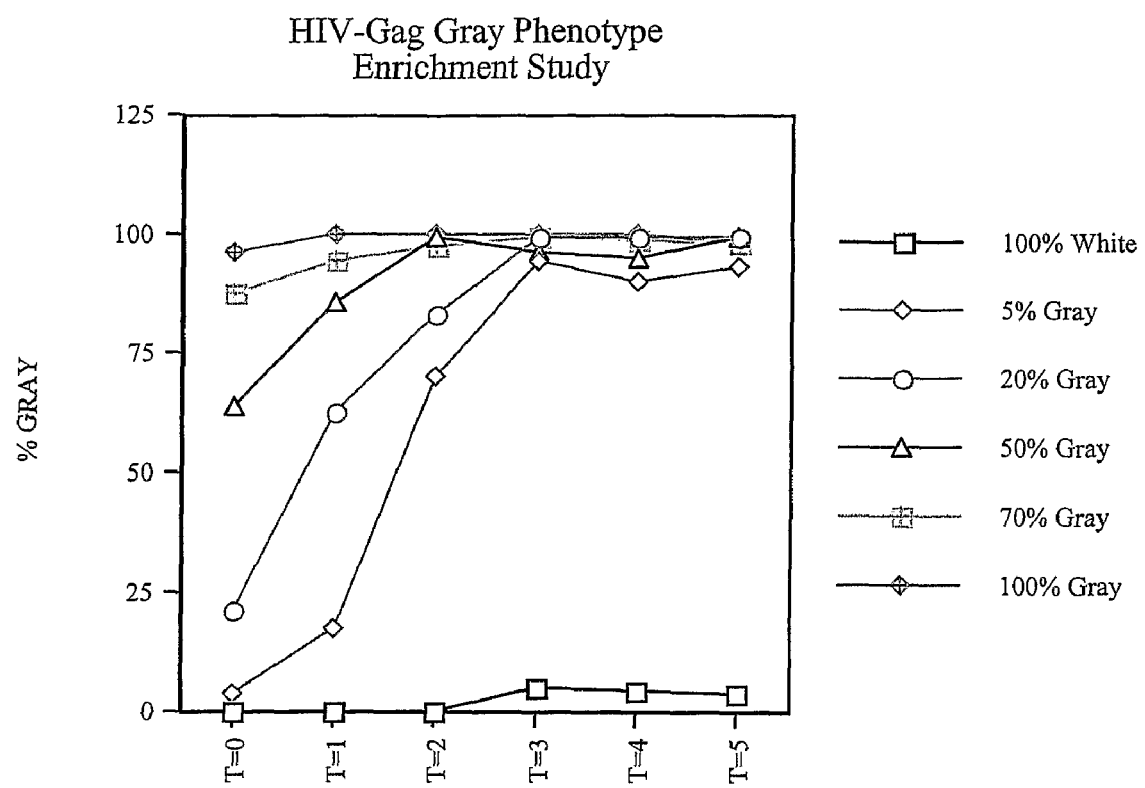
FIG. 2 shows the results of a kinetic enrichment study using a HIV-Gag DNA plasmid. Varying ratios of white:gray phenotypic colonies were used to inoculate chemically-defined medium. This figure shows the percentage of gray-colored colonies identified by the blood agar phenotype screening assay present in the cultures over the course of five enrichment steps. After the third enrichment, the resulting cell populations consisted of greater than 95% gray phenotypic colonies in all the test flasks.

The present invention describes a fermentation process that combines the benefits received from pre-selecting high producing bacterial clones with those related to cultivating bacteria under a limited nutrient feeding regime in a chemically-defined medium. Novel methods of selecting for highly productive clones of E. coli for the production of plasmid DNA, including but not limited to the production of plasmid DNA on a large scale, are disclosed. The process disclosed herein comprises the selection of highly productive clonal subtypes of E. coli cells capable of generating larger quantities of plasmid DNA per cell in comparison to non-selected, transformed cells; followed by the cultivation of said bacterial clones under a fermentation regime in a chemically-defined medium with limited nutrient feeding. Said fermentation regime ensures amplified plasmid productivity with a high cell density. The resulting process is highly productive, generating record high volumetric productivity in the order of 1-1.5 gram of plasmid/L, scalable and reproducible. Achieving high specific productivity (i.e., copy number per cell) and high yield of plasmid during the fermentation process is an important factor contributing to the efficient downstream purification of said plasmid DNA.

The present invention relates to a process for the production of plasmid DNA comprising a first step of selecting a highly productive clonal subtype of a strain of E. coli harboring a DNA plasmid, wherein said highly productive clonal subtype exhibits a higher plasmid copy number per cell in comparison to non-selected, transformed E. coli clonal subtypes of the same strain. This selection process is exemplified herein, in both the specification and the Examples, using the DH5 strain of *E. coli*; however, this exemplification is not intended to limit the scope of the present invention to the use of *E. coli* DH5 cells solely for the fermentation process described herein. It will be known to one of skill in the art that alternate strains of *E. coli* can be furnished for use in the DNA production process of the present invention.

The present invention is partly based upon the observation that *E. coli* DH5 cells transformed with a number of plasmid DNA vaccine candidates displayed culture heterogeneity, exhibiting two colony phenotypes with distinct morphologies when plated on differential and/or chemically-defined agar medium. Colony isolation and subsequent testing of each phenotype led to the discovery of specific phenotypic clonal isolates capable of increased plasmid amplification during fermentation, generating high quantities of clinical-grade plasmid DNA. Thus, the present invention describes a new fermentation process comprising a first step of selecting for highly productive clonal isolates of a strain of *E. coli*, including but not limited to the DH5 strain, for production of plasmid DNA.

The highly productive clonal isolates selected by the methods described in the present invention are subjected to a fermentation process, including but not limited to a commercial fermentation process of a large scale, employing a limited nutrient feeding regime in a chemically-defined medium. *E. coli* is a non-fastidious microorganism that can grow both in rich complex organic media as well as salt-based chemically-defined media supplemented with an organic carbon source. Cultivation medium composition can both directly dictate biomass production and influence the microorganism's regulatory system, affecting plasmid volumetric yield (i.e., gram of plasmid per liter of medium) and specific yield (i.e., plasmid copy number per cell), respectively. Bacterial fermentation processes for the production of laboratory-scale DNA vaccine production generally employ a batch process in a complex and rich medium using either large shake flasks or small laboratory fermentors. Advantages of complex media are that the constituent raw materials are inexpensive, readily available and form a complete or nearly complete nutrient source for the microorganism. Batch fermentation also allows bacterial host cells to grow at a fast rate. However, complex fermentation media have several important disadvantages, especially for a large-scale commercial operation. Most importantly, complex raw materials have a chemically-undefined composition with a variable quality. A high oxygen supply is required when using complex medium for bacterial fermentation, along with high agitation speeds, aeration rates and pressures during large-scale fermentation. Foaming often occurs, due mainly to poor oxygen transfer, resulting in low plasmid productivity and inconsistent results. Thus, these fermentation regimes yield a low cell mass, ranging from 1 to 7 gram dry cell weight/liter, and modest plasmid yields only suitable for studies employing a limited number of small animals (see, for example, Diogo, M. et al., 2000, *Biotechnol. Bioeng.* 68:576-583; Diogo, M. et al., 2001, *J. Gene Med.* 3:577-584; Drew, D. et al., 2000, *Vaccine* 18:2522-2532; Wang, Z. et al., 2001, *Process Biochem.* 36:1085-1093; and Reinikainen, P. et al., 1989, *Biotechnol. Bioeng.* 33:386-393).

The present invention resolves the above problems by cultivating pre-selected, high-producing bacterial clones using a continuous feeding regime in a chemically-defined medium. In the past, product yields obtained using chemically-defined media on an industrial scale were typically considered to be substantially lower than those obtained using media containing complex raw materials. Thus, chemically-defined media have classically been applied to plasmid DNA production for either research purposes only or fermentation processes of a relatively small scale. The present invention describes a fermentation process for the generation of plasmid DNA using chemically-defined medium that yields record amounts of product, even with industrial-scale production processes. This process tolerates manageable operation conditions (e.g., agitation speed and aeration rate) since a reduced culture growth rate is achieved by controlled feeding of the key nutrient. While cell growth rate is greatly reduced during the nutrient feeding period, intracellular plasmid replication continues. Thus, the present invention describes a defined medium fermentation regime which maintains a high specific productivity. By controlling the microorganism's specific growth rate, the cell switches its internal cellular mechanisms from biomass generation to plasmid or protein production, resulting in amplified specific productivity (i.e., plasmid copy number per cell) (see Chen, W. et al., 1997, *J. Ind. Microbiol. Biot.* 18:43-48; Riesenberg, D. et al, 1991, *J. Biotechnol.* 20:17-28). Chemically-defined media formulations also permit extensive analytical investigations, such as metabolic and quality control studies, and will be helpful in achieving a better position with respect to the regulatory environment by supporting safety and reproducibility claims, an important factor when designing a process for the production of plasmid DNA for genetic vaccination and gene therapy purposes.

The present invention is drawn to a process for the production of plasmid DNA, including but not limited to the production of plasmid DNA on a large scale, which results in a record high yield of product. This process comprises selecting a highly productive clonal subtype of a strain of *E. coli*, including but not limited to the DH5 strain, harboring a DNA plasmid, wherein a highly productive clonal subtype exhibits a higher plasmid copy number per cell in comparison to similarly tested, non-selected, transformed *E. coli* clonal subtypes of the same strain. A highly productive clonal subtype selected as described herein is then cultivated with fed-batch fermentation in chemically-defined medium. The present invention further relates to a fermentation process as described above wherein said selection process to identify highly productive clonal subtypes of a strain of *E. coli* containing a DNA plasmid comprises a first selection step wherein potential highly productive clonal subtypes of *E. coli* are isolated; followed by a second selection step wherein said potential highly productive clonal subtypes previously isolated are evaluated in a small-scale fermentation system to determine which clonal subtypes are highly productive. In the two-step selection process to identify a highly productive clonal subtype of *E. coli* described herein, the first selection step comprises the identification and subsequent purification of potential highly productive clonal subtypes of a strain of *E. coli*, including but not limited to the DH5 strain. In this first selection step, the pool of *E. coli* clonal subtypes, comprised of bacterial cells transformed with a DNA plasmid of interest, is reduced to include only those clonal variants that have the possibility of demonstrating an ability to generate a higher plasmid copy number per cell in comparison to the other transformed *E. coli* cells grown under similar fermentation conditions. Thus, the potential highly productive clonal subtypes of *E. coli* of the present invention have the potential of exhibiting a higher than normal specific productivity (i.e., plasmid copy number per cell).

In one embodiment of the present invention, a method of selecting for potential highly productive clonal subtypes of a strain of *E. coli*, including but not limited to the DH5 strain, transformed with a DNA plasmid of interest comprises first observing a phenotypic heterogeneity in the colonies generated by said *E. coli* strain on agar medium; followed by the purification of those colonies that represent a minor component of the population of colonies generated by the transformed bacterial cells. One of skill in the art can easily identify when phenotypic heterogeneity, including but not limited to heterogeneity in morphological, physiological and/or biochemical characteristics, is present in a population of colonies of transformed bacterial cells. Said phenotypic heterogeneity may be due to a number of different factors, including but not limited to the presence of a clonal variant of the original bacterial strain possibly generated, for example, during the transformation process. If the phenotypic heterogeneity is due to the presence of a subtype of the original bacterial strain, one of skill in the art will appreciate the potential of said phenotypic variant representing a clone of the original bacterial strain possessing altered growth characteristics, including but not limited to the characteristic of increased plasmid amplification.

Bacterial clonal subtypes have been described in the scientific literature. Phenotype switching in *Candida albicans* occurs as a direct result of differential gene expression (Soll, D. et al., 1995, *Can. J. Bot.* 73:1049-1057). Two opaque-specific genes, PEP1 and OP4, and one white-specific gene, WH11, are responsible for the white to opaque phenotype switching in pathogenic *Candida*. While this is associated with virulence in *Candida*, a similar phenomenon may exist in selecting bacterial clones with superior specific productivity. Colony variants have also been identified for pathogenic strains of *Neissetia meningitidis*. In this case, phenotype diversity is associated with intra-strain heterogeneity of lipopolysaccharides and class-5 outer membrane proteins (Poolman, J. T. et al., 1985, *J. Med. Microbiol.* 19:203-209). The effects of plasmid presence on the growth and enzymatic activity of *E. coli* DH5 has also been described by Mason, C. A. et al. (1989, *Appl. Microbiol. Biotechnol.* 32:54-60), demonstrating that plasmid copy number has a direct effect on the expression of host cell enzymes involved in carbon metabolism. Thus, the generation of *E. coli* clonal subtypes with different growth characteristics may result from of a variety of different events, including but not limited to mutations induced by the DNA transformation process or stress imposed by cultivating the bacteria in a selectively enriched medium.

Once a potential highly productive clonal isolate of *E. coli* containing a DNA plasmid of interest is identified and purified as described herein, the second step of the selection process is to evaluate each potential highly productive clonal subtype to determine which clonal subtypes are indeed highly productive. In one embodiment of the present invention, a small-scale fermentation system is used to test the productivity of said potential highly productive clonal subtypes isolated in step one of the selection process, ultimately identifying the clonal isolates isolated from round one of said selection process that generate a higher plasmid copy number per cell in comparison to non-selected *E. coli* cells transformed with the same DNA plasmid and grown under similar fermentation conditions. If a highly productive clonal subtype identified via this selection process is to be used in a large-scale fermentation regime for the production of commercial quantities of plasmid DNA, said small-scale fermentation system will simulate the fermentation conditions of the subsequent large-scale fermentation process. The specific productivity of non-selected *E. coli* cells (i.e., clonal isolates of *E. coli* that are not selected in the first round of the selection process described herein), including but not limited to DH5 cells, harboring a DNA plasmid can be readily determined by calculating the average productivity of a population of clonal isolates of said bacterial strain.

One of skill in the art will recognize that bacterial clonal variants of the present invention may be identified in a number of different ways, including but not limited to observing a phenotypic (e.g., morphological) heterogeneity in a population of bacterial colonies plated on differential agar. In one embodiment of the present invention, potential highly productive clonal isolates of transformed *E. coli* DH5 cells form phenotypically gray-colored colonies when plated on blood agar. Said gray colonies appear irregularly shaped, flat and translucent. In comparison, the colonies formed by the major component of the population of transformed *E. coli* DH5 cells are white in color when plated on blood agar, circular in shape, and raised with a smooth texture. Said potential highly productive clonal isolates of *E. coli* DH5 that form gray-colored colonies on blood agar were initially identified when performing routine culture purity tests on final fermentor broth samples for Good Manufacturing Practice ("GMP") fermentations of influenza DNA vaccine candidates. A heterogeneous population of gray- and white-colored colonies was visible on blood agar plates. It was determined that the gray-colored colonies became the dominant phenotype in the fermentation broth samples. Clonal isolates of the gray- and white-colored colony-producing cells were purified and characterized for growth kinetics and plasmid productivity. A correlation was identified between the clonal isolates that generate the gray phenotypic colonies and an increased specific productivity when compared to clonal isolates generating the white-colored colonies.

The gray phenotypic colonies of transformed *E. coli* DH5 cells of the present invention which represent potential highly productive clonal isolates of said cells are distinguishable from the non-selected, white-colored DH5 colonies of the same strain when visualized on blood agar. Blood agar is a general purpose, non-selective, non-defined medium for the cultivation of fastidious and non-fastidious microorganisms. Blood agar plates typically contain 5% sheep's blood (by volume) and either a Columbia agar or a tryptic soy agar base. It is readily apparent to those skilled in the art that agar plates used to distinguish between two colony phenotypes should be incubated under conditions that facilitate bacterial colony formation. Said growth conditions can vary, for example, in incubation temperature, as well as in length of time of incubation. The incubation time and temperature may be adjusted according the conditions empirically determined to facilitate greatest visual distinction between the alternate colony phenotypes. In one embodiment of the present invention, potential highly productive clonal isolates of a strain of *E. coli*, including but not limited to *E. coli* DH5, are identified as gray-colored colonies when plated on 5% Columbia sheep's blood agar. Preferred incubation conditions to maximize the phenotypic differences between the gray- and white-colored DH5 colonies on blood agar is an incubation temperature of about 30° C. for a time period of about 48 hours; however, one of skill in the art can appreciate that these numbers are not strict guidelines.

In order to evaluate the growth characteristics of potential highly productive clonal isolates of the present invention, it is first necessary to purify said bacterial clones away from non-selected, transformed cells (i.e., those that produce white-colored colonies on blood agar). A clonal isolate represents a pure culture of a subtype of an original bacterial cell of interest. Thus, pure cultures are populations of cells arising from a single cell. When a mixture of cells is either spread or streaked onto an agar surface so that a single bacterial cell generates a completely separate colony, said colony represents a pure culture. Usually, said pure culture can be isolated, and subsequently propagated, by picking the single colony and re-spreading/re-streaking said colony onto another agar plate. Thus, one of skill in the art will appreciate that if multiple bacterial colonies come into contact with each other on an agar plate, repeated purification techniques using a spread plate or streak plate process will eventually result in the purification of a pure culture.

In one embodiment of the present invention, potential highly productive clonal isolates of *E. coli* DH5 can be identified on blood agar because said clonal subtypes form gray-colored colonies in comparison to the white-colored colonies formed by the non-selected, transformed DH5 cells. However, said gray colonies, representing potential highly productive clonal isolates, are indistinguishable from colonies of non-selected, transformed DH5 cells when plated on chemically-defined agar medium. The potential highly productive clonal subtypes of the present invention that form gray-colored colonies on blood agar can be purified directly from said blood agar plates. Alternatively, it may be desirable to avoid all contact between the highly productive clonal isolates used in the final plasmid DNA production process of the present invention and any blood products. To purify potential highly productive clonal subtypes of a strain of *E. coli* that form phenotypically unique colonies on blood agar, for example, the gray-colored colonies as described herein, whereby the ultimate clonal subtype to be used in a final fermentation process has failed to contact any blood products, a duplicate plating technique can be utilized. A duplicate plating technique requires that the initial transformed *E. coli* cells, in additional to any subsequent purification intermediate, is duplicate plated on blood agar and a second type of agar medium, including but not limited to a chemically-defined agar medium. Once a heterogeneous population of phenotypically distinct colonies is visible on said blood agar plate, for example, a mixture of gray- and white-colored DH5 colonies, single colonies from the corresponding second agar plate are picked and re-spread/re-streaked onto both types of agar media. This selection and purification process is continued until the blood agar plate contains a uniform population of phenotypically distinct and unique colonies, for example, gray-colored colonies, whereby single colonies from the corresponding second agar medium represent potential highly productive clonal isolates that have never contacted blood products. In one embodiment of the present invention, the second agar medium described above is DM-P5 chemically-defined agar medium, described infra in Example 1. Once a clonal isolate of the present invention is purified, said cells may be periodically re-evaluated on blood agar, testing the purity of the culture.

The first step of the process for plasmid DNA production described herein comprises selecting a highly productive clonal subtype of a strain of *E. coli*, including but not limited to the DH5 strain, harboring a DNA plasmid, wherein said first step of the selection process is to identify and purify potential highly productive clonal subtypes of said strain that form phenotypically gray-colored colonies when plated on blood agar. The present invention further relates to a method for selecting a highly productive clonal subtype of a strain of *E. coli*, including but not limited to the DH5 strain of *E. coli*, for plasmid DNA production comprising the steps of: (a) purifying colonies of a strain of *E. coli* harboring a DNA plasmid that are phenotypically gray on blood agar, wherein a gray-colored colony represents a potential highly productive clonal subtype; and, (b) testing productivity of said potential highly productive clonal subtypes, wherein a highly productive clonal subtype exhibits a higher plasmid copy number per cell in comparison to non-selected, transformed *E. coli* clonal subtypes of the same strain tested under similar fermentation conditions. In one embodiment of the present invention, the blood agar plates of said described method are incubated for about 48 hours at about 30° C.

Another embodiment of the present invention comprises a method for selecting a highly productive clonal subtype of a strain of *E. coli*, including but not limited to the DH5 strain of *E. coli*, for production of plasmid DNA comprising the steps of: (a) plating a strain of *E. coli* harboring a DNA plasmid on both blood agar and chemically-defined agar medium and incubating said plates until bacterial colonies form; (b) picking individual colonies from the chemically-defined agar medium plate of which the corresponding blood agar plate contains a population of colonies with a gray phenotype; (c) purifying individual colonies from step (b) on both blood agar and chemically-defined agar medium plates until the blood agar plate contains a uniform population of phenotypically gray colonies; (d) picking individual colonies purified in step (c) from the chemically-defined agar medium plate, said colonies representing potential highly productive clonal subtypes; and, (e) determining productivity of said potential highly productive clonal subtypes, wherein a highly productive clonal subtype exhibits a higher plasmid copy number per cell in comparison to non-selected, transformed *E. coli* cells of the same strain under similar fermentation conditions. In one embodiment of the present invention, the chemically-defined agar medium described above is DM-P5 chemically-defined agar medium, described infra in Example 1.

One of skill in the art will recognize that many different selection strategies are available to isolate potential highly productive bacterial clones of the present invention. One such strategy is described above, developed after observing that transformed *E. coli* DH5 cells may produce a heterogeneous population of phenotypically gray- and white-colored colonies on blood agar. While optimizing the fermentation regime for a number of DNA vaccine candidates, it was also observed that colonies formed from an initial transformed, recovered DH5 cell population displayed two distinct phenotypes on chemically-defined agar medium, DM-P5, described infra in Example 1, after extending the incubation period to about 5 days at about 37° C. Cream-colored colonies and cream-colored colonies containing brown centers were detected. It was later determined that clonal isolates generated from the cream-colored colonies have the potential of generating gray phenotypic colonies, described infra, when plated on blood agar. Thus, said cream-colored colonies represent a subset of *E. coli* DH5 cells transformed with a DNA plasmid that have the potential of being identified as highly productive clonal subtypes as per the present invention. It has been observed that clonal isolates exhibiting the cream-colored colony phenotype on DM-P5 selective agar medium can give rise to a mixed population of both the white and gray phenotypic colonies when plated on blood agar. However, no transformed DH5 clonal isolate that generates cream-colored colonies with brown centers have shown the ability to produce high plasmid DNA titers or to give rise to gray phenotypic colonies on blood agar.

The present invention relates to a fermentation process as described herein comprising a first step whereby a highly productive clonal subtype of a strain of *E. coli*, including but not limited to the DH5 strain of *E. coli*, harboring a DNA plasmid is selected on chemically-defined medium, said selection process comprising a first selection step wherein potential highly productive clonal subtypes of *E. coli* are isolated. As described above, this first selection step reduces the pool of *E. coli* clonal subtypes of interest, comprised of bacterial cells of a particular strain transformed with a DNA plasmid, to those clones with the possibility of demonstrating an ability to generate a higher plasmid copy number per cell in comparison to non-selected, transformed *E. coli* cells of the same strain grown under similar fermentation conditions. One embodiment of the present invention represents a method of selecting for said potential highly productive clonal subtypes of a strain of *E. coli*, including but not limited to the DH5 strain, transformed with a DNA plasmid of interest comprising first observing a phenotypic heterogeneity in the colonies generated by said bacterial cells when plated on differential and/or chemically-defined agar medium, followed by the purification of those colonies which represent a minor component of the population of colonies generated by said transformed cells. In a further embodiment of the present invention, said potential highly productive clonal subtypes are phenotypically cream on chemically-defined agar medium that has been incubated until a population of both cream-colored colonies and cream-colored colonies with brown, bulls-eyed centers have formed. In a further embodiment of this aspect of the present invention, said cream-colored colonies are formed after incubating said chemically-defined agar medium at about 37° C. for about 5 days.

The present invention further relates to a method for selecting a highly productive clonal subtype of a strain of *E. coli*, including but not limited to the DH5 strain of *E. coli*, for plasmid DNA production comprising the steps of: (a) incubating a strain of *E. coli* harboring a DNA plasmid plated on chemically-defined agar medium until a population of both cream-colored colonies and cream-colored colonies with brown, bulls-eye centers have formed; (b) purifying said cream-colored colonies from step (a), wherein a cream-colored colony represents a potential highly productive clonal subtype; and, (c) testing productivity of said potential highly productive clonal subtypes, wherein a highly productive clonal subtype exhibits a higher plasmid copy number per cell in comparison to non-selected, transformed *E. coli* cells of the same strain tested under similar fermentation conditions. In a further embodiment of the present invention, the chemically-defined agar medium used in this method of selection, including but not limited to DM-P5 selective agar medium, described infra, is incubated at about 37° C. for about 5 days.

Another embodiment of the present invention comprises a method of selecting a highly productive clonal subtype of a strain of *E. coli*, including but not limited to the DH5 strain of *E. coli*, for plasmid DNA production comprising the steps of: (a) incubating a strain of *E. coli* harboring a DNA plasmid plated on chemically-defined agar medium until a population of both cream-colored colonies and cream-colored colonies with brown, bulls-eye centers have formed; (b) picking cream-colored colonies from step (a); (c) plating cells of said cream-colored colonies picked in step (b) on both blood agar and chemically-defined agar medium; (d) picking individual colonies from the chemically-defined agar medium of which the corresponding blood agar plate contains a population of colonies with a gray phenotype; (e) purifying individual colonies from step (d) on blood agar and chemically-defined agar medium until the blood agar plate contains a uniform population of phenotypically gray colonies; (f) picking individual colonies purified in step (e) from the chemically-defined agar medium, said colonies representing potential highly productive clonal subtypes; and, (g) testing productivity of said potential highly productive clonal subtypes, wherein a highly productive clonal subtype exhibits a higher plasmid copy number per cell in comparison to similarly tested, non-selected, transformed *E. coli* cells of the same strain. In one embodiment of the present invention, the chemically-defined agar medium described in step (a) above, including but not limited to DM-P5 agar medium, described infra, is incubated at about 37° C. for about 5 days; however, one of skill in the art will appreciate both that these incubation parameters are mere guidelines and how these guidelines can be altered to achieve a similar result.

When initially observing the presence of a heterogeneous population of transformed *E. coli* cells, e.g., by visibly identifying bacterial colonies generated from said transformed cells on an agar medium displaying alternate morphological phenotypes, it is important to assess whether the apparent bacterial variants are indeed subtypes of said transformed *E. coli* cells and not mere contaminants. Possible contaminants may originate from foreign bacterial or non-bacterial sources. Additionally, when selecting for highly productive clones of a transformed bacterial strain for the production of plasmid DNA, it is essential to confirm that said plasmid is indeed contained within said bacterial cell. One of skill in the art will recognize that there are many ways to identify both foreign bacterial or non-bacterial contaminants, including but not limited plating clonal isolates on differential agar and performing fatty acid methyl ester ("FAME") analysis. Many techniques also exist to detect plasmid DNA within bacterial cells, including but not limited to performing agarose gel electrophoresis of bacterial cell lysates or plating said bacteria on antibiotic containing agar medium corresponding to the antibiotic resistance gene within the plasmid. For example, in the present invention, purified, DH5 clonal isolates (i.e., those that formed either gray-colored or white-colored colonies on blood agar) were plated onto the following types of agar medium: DM-P5, see infra, containing neomycin since the plasmid in said clones contained a neomycin resistance marker; DM-P5 lacking neomycin; and LES Endo and Levine EMB, *E. coli* selective agar media used to distinguish and identify gram negative *Enterobacteriaceae* growth. Of the approximately 50 clonal isolates tested, all contained the plasmid conferring resistance. The clonal isolates tested also exhibited typical growth patterns for *E. coli*, particularly of the DH5 strain, showing an excellent *E. coli* profile match by FAME analysis.

After selecting potential highly productive clonal subtypes of *E. coli* harboring a DNA plasmid of the present invention, the present invention includes evaluating said clonal subtypes to determine which clones identified from the first selection step possess a specific productivity greater than that of non-selected *E. coli* cells of the same strain, transformed with the same plasmid, and grown under similar fermentation conditions. In one embodiment of the present invention, the potential highly productive clonal isolates are evaluated using a small-scale fermentation system. The size of the small-scale fermentation system will depend upon the size of the ultimate fermentation process to be used for the selected, highly productive clonal subtypes described herein. If, for example, the highly productive clonal subtype of *E. coli* selected via the methods of the present invention is to be used in a fermentation process for large-scale production of plasmid DNA, a small-scale fermentation system in which to evaluate the potential highly productive clonal subtypes comprises a system that cultivates said bacterial isolates in flasks ranging from about 250 mL to about 2 L in size. Additionally, said potential highly productive clonal isolates are evaluated using a fermentation regime that simulates the final commercial, large-scale fermentation process. The small-scale fermentation system will allow for rapid screening of the potential highly productive clones and will generate productivity data that are consistent with the final fermentation process that will be used to generate the plasmid DNA. Likewise, if a selected, highly productive clonal subtype of *E. coli* is to be used in a smaller scale DNA production process, the small-scale fermentation regime of the present invention used to evaluate the productivity of the potential highly productive clonal subtypes isolated in step one of the selection process will comprise a system that cultivates the clonal subtypes in a smaller fermentation vessel than that which will be used in the final fermentation process. Again, the small-scale fermentation system will simulate the fermentation conditions of the ultimate fermentation regime for the production of plasmid DNA.

In one embodiment of the present invention, the potential highly productive clonal isolates described herein are evaluated using a shake flask with feeding ("SFF") fermentation system whereby each flask is supplemented with continuous feeding. A SFF system represents a small-scale fermentation system wherein said clonal isolates are cultivated in a baffled shake flask no larger than about 1000 mL, and preferably, a 250 mL baffled shake flask. A highly productive clonal variant of the present invention that is identified after being evaluated in a SFF system, as described herein, can be used for the production of plasmid DNA in a large-scale, commercial fermentation process. In one embodiment of the present invention, the flasks of the SFF system used to evaluate the potential highly productive clonal isolates of $E.$ $coli$, including but not limited to DH5 cells described herein, are continuously fed with a dilute glycerol/monosodium glutamate ("MSG") mixture, preferably a feed solution comprising about 4.6% glycerol (v/v) and about 2.9% MSG (w/v). Feeding is preferably initiated during the exponential growth phase of the bacteria (i.e., mid-logarithmic phase of growth) and mimics the fed-batch process used in the ultimate, large-scale fermentation process. Additionally, a slow feed strategy is used, preferably wherein said feed solution is delivered at approximately 6.4 µl/hour/mL broth, forcing the cells to grow in a slow, linear fashion. Again, this simulates the large-scale fermentation process. A preferable SFF system used to evaluate the clonal isolates selected via the methods described herein does not require pH control as it is impractical for a shake flask system. Preferably, a SFF system described herein will be properly synchronized in order to screen as many potential highly productive clonal isolates as possible. Additionally, because of the inherent oxygen limitation in a shake flask, the clonal isolates tested in this manner are preferably cultivated in a medium that supports a relatively low biomass without feeding. Therefore, when feeding is initiated, biomass can rise significantly without the culture becoming oxygen limited. In one embodiment of the present invention, the potential highly productive clonal isolates described herein are cultivated in a chemically-defined medium related to DM-P5 medium, DME-B12 medium (see infra Example 3 for specific composition).

In one embodiment of the present invention, after evaluating the characteristics of the potential highly productive clonal subtypes of the present invention and determining which clonal subtypes identified and purified in round one of the selection process demonstrate a high specific productivity, as described supra, a highly productive clonal subtype is then cultivated with fed-batch fermentation in chemically-defined medium. Said highly productive clonal subtypes can be cultivated on an industrial scale, increasing the yield of large-scale production of plasmid DNA. Industrial- or large-scale microbial cell fermentation, as used herein, is considered to have a total fermentation volume greater than standard laboratory bioreactors which generally accommodate fermentation volumes of approximately 200 L, 500 L or 1000 L. Industrial- or large-scale microbial cell bioreactors can accommodate total fermentation volumes of greater than about 1000 L, and can include fermentation vessels as large as 10,000 to 100,000 L.

Two distinct fermentation technologies, batch and fed-batch, have been employed for plasmid over-production in $E.$ $coli$ (see, for example, Riesenberg, D., 1991, $Curr.$ $Opin.$ $Biotechnol.$ 2:380-384; Yee, L and H. Blanch, 1992, $Biotechnol.$ 10: 1550-1556; and Lee, S. Y., 1996, $TIBTECH$ 14:98-105). Typically, batch fermentation is a cell culture process by which all the nutrients required for both cell growth and plasmid production are present in the fermentation vessel in great excess at the time of inoculation, obviating the need to make additions to the vessel. In batch fermentation, the growth rate is controlled through manipulation of environmental parameters (e.g., temperature, pH, oxygen supply) and the carbon source. Batch fermentation is severely limited with respect to achieving high biomass cultures, contributing to the generation of low plasmid volumetric yields. In a fed-batch process, either none or part of the compounds comprising one or more of the structural and/or catalytic elements of the fermentation medium is added to the fermentor in the initial phase of the fermentation process. Once the cells have attained a desired density, either all or the remaining part, respectively, of the compounds comprising one or more of the structural and/or catalytic elements is then fed to the fermentor. In fed-batch fermentation, the cell growth rate is controlled by the addition of these nutrients to the culture over an extended period of time. The compounds which are selected for feeding can be fed together or separate from each other. In a repeated fed-batch and a continuous fermentation process, the complete start medium is additionally fed during this fermentation stage. In a repeated fed-batch process, part of the fermentation broth comprising the biomass is removed at regular time intervals, whereas the removal of part of the fermentation broth occurs continuously in a continuous fed-batch fermentation process. The fermentation process is thereby replenished with a portion of fresh medium corresponding to the amount of withdrawn fermentation broth.

By controlling nutrient availability to a level compatible with oxygen transfer capabilities of the fermentation vessel, accumulation of toxic by-products due to the creation of an oxygen-limited environment is avoided when using a fed-batch fermentation system. A desired growth rate is achieved by creating a constant environment through a tailored feeding regimen, using either a constant feed rate or following sophisticated feeding algorithms. Plasmid copy number can be positively influenced by maintaining a down-regulated growth rate, called plasmid amplification (see Reinikainen, P. et al., 1989, $Biotechnol.$ $Bioeng.$ 33:386-393; Namdev, P. K., 1993, $Biotechnol.$ $Bioeng.$ 41:660-670; Schmidt, T. et al, 2001, $P/ace$ $setter$ 5:4-6; and Chen, W. C., 1997, $J.$ $Indust.$ $Microbiol.$ $Biotechnol.$ 18:43-48). It is thought that this higher plasmid content is due to both greater plasmid stability and favored plasmid synthesis over other biochemical pathways. Thus, a two-phase strategy is often employed in productive plasmid DNA processes: (1) a biomass build-up phase where the cells grow exponentially; and (2) a slow growth phase achieved by fed-batch methodologies wherein plasmid amplification occurs. Importantly, each recombinant construct also presents its own limitations.

A fermentation vessel contains the cultured cells submerged in a liquid nutrient medium. Cultivating medium is typically sterilized either before or after introduction into the fermentation vessel. In some cases, certain components of the medium cannot be sterilized together as chemical intermediates may form between certain components of the medium during heat sterilization, altering the composition of the medium and the concentration of certain nutrients in said medium. In these cases, the medium may be prepared as two or more separate media, wherein known incompatible components are kept apart during sterilization. These separate media can then be combined after sterilization to create the complete, sterile medium. Additionally, some substances, particularly certain proteins, are not amenable to heat sterilization as they may be heat-denatured. This can be avoided by filter sterilizing these substances before adding them to the cultivation medium.

The fermentation vessel is usually equipped with a means to oxygenate the cells in solution. Typical means to oxygenate the tank include a stirring mechanism which is often part of the fermentation vessel itself or an inlet wherein air or oxygen is pumped into the vessel. Aside from a means to aerate the cultured cells, other useful components contained on the fermentation vessel and used in the present invention include, without limitation, probes for pH, dissolved oxygen and temperature measurements, a pressure sensor, as well as one or more ports for the addition of nutrient and/or other solutions.

The present invention relates to a fermentation process for the production of plasmid DNA comprising the steps of first selecting a highly productive clonal subtype of a strain of $E.$ $coli$ harboring a DNA plasmid, as described supra, and then cultivating said highly productive clonal subtype with fed-batch fermentation. In one embodiment of the present invention, said highly productive clonal subtype is cultivated using a large-scale fermentation process. Both the selection process and the final fermentation regime of the present invention is executed using chemically-defined media. The chemically-defined media described herein have been designed to support the over-production of plasmid DNA. As used herein, the term "chemically-defined" media is understood to be media which are essentially composed of chemically-defined constituents. A fermentation medium which is essentially composed of chemically-defined constituents includes a medium which does not contain a complex carbon and/or nitrogen source. Therefore, a chemically-defined medium essentially does not contain undefined nitrogen (e.g., animal or plant protein, or protein hydrolysate compositions) or carbon sources (e.g., molasses or corn steep liquor). Instead, the nitrogen sources are well-defined inorganic or organic compounds, and the carbon source is a well-defined sugar. Additionally, a chemically-defined medium contains mineral components, such as salts, e.g., sulfates, phosphates and chlorides of alkaline and earth alkaline metals, and micronutrients.

One embodiment of the present invention relates to a series of chemically-defined medium formulations which comprise a salt component of potassium phosphate monobasic ($KH_2PO_4$), potassium phosphate ($K_2HPO_4$) and ammonium sulfate (($NH_4)_2SO_4$). In a further embodiment, said salt component of the disclosed chemically-defined media optionally includes sodium chloride (NaCl). A particular embodiment of the present invention relates to a chemically-defined medium which comprises about 7.0 g/L $KH_2PO_4$, about 7.0 g/L $K_2HPO_4$ and about 6.0 g/L $(NH_4)_2SO_4$, and optionally comprises about 0.5 g/L NaCl.

In a further embodiment of the present invention, said chemically-defined medium used for the selection and/or fermentation steps of the plasmid DNA production process disclosed herein comprises a salt component, as described above, in addition to a carbon source, including but not limited to glycerol, and/or a nitrogen source, including but not limited to monosodium glutamate ("MSG") and L-glutamic acid. MSG is the sodium salt of L-glutamic acid. A particular embodiment of the present invention relates to a chemically-defined medium which comprises a salt component, as described herein, in addition to glycerol used as a carbon source, preferably at a concentration of about 10.0-15.0 g/L, and more preferably 15.0 g/L. Another particular embodiment of the present invention relates to a chemically-defined medium which comprises a salt component and a carbon source as described herein, in addition to a nitrogen source of MSG or L-glutamic acid at a concentration of about 5.0 g/L. In a still further embodiment of the present invention, said chemically-defined medium on which the highly productive clonal isolates of the present invention are selected and then later used for cultivation of said bacterial clones optionally comprises one or more of the following components: ucon, thiamine hydrochloride, $MgSO_4.7H_2O$, neomycin sulfate and trace elements.

A chemically-defined medium of the present invention used to select and/or cultivate highly productive $E.$ $coli$ cells described herein includes, but is not limited to, a medium selected from the group consisting of DM-P5, DME-B12, Medium C, Medium D, Medium E, Medium F and Medium G (see infra Examples section for specific media compositions and preparation). It will be appreciated that these media are only examples. A person of skill in the art will be able to provide alternative chemically-defined media which permit selection and/or cultivation of highly productive $E.$ $coli$ cells, including but not limited to DH5 cells, harboring a DNA plasmid as described in the novel processes disclosed herein. As such, the present invention is not limited to use of the specific media compositions described and exemplified herein but is meant to include additional, non-exemplified chemically-defined media compositions which will be amenable to the selection and/or cultivation of highly productive clonal isolates of $E.$ $coli$ harboring a DNA plasmid. In one embodiment of the present, said chemically-defined medium used to cultivate a highly productive clonal subtype of $E.$ $coli$ identified as per the methods described herein is formulated to support fermentation of said bacteria on a large scale.

The DNA plasmid vector cultivated by the methods described in the present invention can be any extra-chromosomal DNA molecule containing a gene(s) encoding a biological compound of interest, i.e. a transgene(s). The plasmid will contain elements required both for its maintenance and propagation in a microbial cell (e.g., $E.$ $coli$), as well as for the subsequent expression of the transgene in the animal host. For bacterial propagation, an origin of replication is needed, in addition to any plasmid encoded function required for replication, such as a selectable marker for selection of successful transformants. For gene expression, the plasmid should be designed to maximize transient production of the transgene upon entry into the animal host. Components of the plasmid contributing to gene expression may include, but is not limited to, a eukaryotic promoter, a transcriptional termination and polyadenylation signal, and an enhancer element(s). A selected promoter for recombinant gene expression in animal cells may be homologous or heterologous, and may be constitutive or inducible, including but not limited to promoters from human cytomegalovirus/immediate-early (CMVIE), simian virus/early (SV40), human elongation factor-1α (EF-1α) and human ubiquitin C (UbC). One of ordinary skill in the art will further recognize how to place these various components on a vector in a particular manner so as to render them functional. Plasmid DNA can be recombinantly engineered using techniques well known to those of ordinary skill in the art, see Sambrook, Fritsch, Maniatis, *Molecular Cloning, A Laboratory Manual*, Second Edition, Cold Spring Harbor Laboratory Press. 1989; and *Current Protocols in Molecular Biology*, Greene Publishing Assoc. & Wiley, 1987; both of which are incorporated by reference herein. Use of low-copynumber vectors is undesirable for plasmid DNA production for polynucleotide vaccination or gene therapy because the product yields will be unfavorably low. The plasmid vector may be transfected or transformed into the host cell using a variety of well known methods such as calcium chloride transfection, electroporation, microinjection and the like.

According to the present invention, the highly productive clonal subtypes of a strain of E. coli identified as per the methods disclosed herein can be cultivated at an industrial-scale for the production of large quantities of plasmid DNA. In such a case, said large-scale fermentation regime is generally initiated by direct inoculation of a seed fermentor, preferably a small flask (i.e., about 250 mL to about 2 liters), containing a starting batch medium with transformed cells, often called the "seed" stage of the fermentation process. If the final fermentation step in which to cultivate the highly productive clonal subtypes of E. coli identified as described herein encompasses a smaller scale fermentation regime, said "seed" stage can consist of directly inoculating a small container of starting batch medium (e.g., a 15 mL sterile tube). The starting batch culture medium will typically contain all nutrients essential for growth and multiplication of the cells. The starting batch culture medium of the present invention is preferably a chemically-defined medium, including but not limited to Medium D, Medium E, Medium F and Medium G (all of which are described infra). The inocula can consist of a thawed aliquot of working seed or large seed stock (see Example 6). The cells in the seed stage are grown to a desired density, and then the contents of the "seed" fermentor are transferred to a production fermentor under sterile conditions, initiating the "production" stage of the fermentation process. For large-scale fermentation regimes, it is the size of the production fermentation that dictates the designation of said fermentation regime as an "industrial-scale" or "large-scale." In one embodiment of the present invention, the timing for transfer between the seed and production fermentation phases is based on the transformed, bacterial cells attaining a mid-logarithmic phase of growth, as determined, for example, by on-line measurements of carbon dioxide evolution rate ("CER"). The cultivation medium of the present invention used in the production stage of fermentation is a chemically-defined medium, including but not limited Medium D, Medium E, Medium F and Medium G. The fermentation conditions of both the seed fermentor and the production fermentor can vary in terms of temperature, airflow rate, agitation speed, vessel pressure and pH. In one embodiment of the present invention, E. coli harboring a DNA plasmid of interest are grown at approximately 37° C. The airflow rate of the seed and production fermentors is preferably set with a range of about 0.25 to 1.00 vvm (volume of air/volume of broth/min). The agitation speed of the seed and production fermentors is preferably sent with a range of about 200 to 800 rpm; however, the agitation speed is dependent on the size of the fermentor, larger vessels requiring lower agitation rates. The pressure of the seed and production fermentors is maintained at a range of about 5 to about 20 PSI. As demand increases during fermentation, the dissolved oxygen level can be maintained by increasing the agitation speed. A dissolved oxygen level of greater or equal to about 30% is preferred, as well as a neutral pH. A neutral pH can be maintained by addition of 25% (v/v) phosphoric acid or 30% (v/v) sodium hydroxide. On-line measurements of dissolved oxygen levels, CER, oxygen uptake rate ("OUR"), pH and cell density of fermentation broth can be made. In an alternative process, the production stage can be directly inoculated from a frozen inoculum source, skipping the seed fermentation step.

The production stage of the fermentation process of the present invention comprises a fed-batch system. A preferred embodiment of the present invention comprises a method of increasing the yield of plasmid DNA production, including but not limited to large-scale production of plasmid DNA, comprising cultivating E. coli DH5 cells harboring a DNA plasmid of interest with a fed-batch fermentation regime, wherein the fed-batch regime is employed at the production stage of the fermentation process. In one embodiment of the present invention, a carbon and/or a nitrogen source is fed to the fermentation vessel at the production stage. A carbon source may include, but is not limited to, glycerol, glucose, fructose, sucrose, maltose, lactose, sorbitol or other simple sugars. A nitrogen source may include, but is not limited to, protein hydrolysates of casein, lactalbumin, albumin, soy protein; meat protein; and, MSG or mixtures of individual amino acids. In one embodiment of the present invention, the carbon source is glycerol, and the nitrogen source is MSG. In another embodiment of the present invention, a feeding solution comprising about 50% glycerol (v/v) and about 25% MSG (w/v) is used. In a further embodiment of the present invention, a feeding solution comprising about 60% glycerol (v/v) is used. In the present invention, once the production stage culture attains logarithmic growth, the carbon and/or nitrogen feeding regimen (timing based on CER) is initiated and continues for about 24-30 hours. The objective of this feeding regimen is to reduce the growth rate, which is conducive to plasmid amplification. A considerably higher amount of carbon and nitrogen supply is tolerated in a fed-batch process as opposed to a batch process. Specifically, the amount of carbon and/or nitrogen source applied in a fed-batch process can be at least about two times higher than the highest amount applied in a batch process. This, in turn, leads to the production of a considerably greater amount of biomass in a fed-batch fermentation process in comparison to a batch fermentation process.

In the present invention, the rate, timing, and volume of delivery of the feed solution into the production stage fermentor of the present invention is typically varied over the course of fermentation. For example, in one embodiment of the present invention, the feed rate is initiated at a lower set point and manually increased over a period of time to a highest value once respiratory activity (measured by CER) has peaked, varying approximately between 2.66 and 3.66 g/L/h. It is preferable that the feeding process results in the cells growing at a linear rate, as opposed to the exponential rate of growth that occurs prior to feeding. The reduced growth achieved during the feeding phase of the fermentation process allows for greater plasmid amplification during fermentation, leading to greater specific productivity and, ultimately, larger DNA plasmid yields. Alternatively, the production fermentor of the present invention can be fed at a constant rate of between about 2.0-12 g/L/h, more preferably at a constant rate not exceeding about 8.0 g/L/h, and most preferably at a constant rate of approximately 8.0 μL/h.

After the cultivation of the E. coli host cells is complete, the plasmid DNA may be obtained from the bacterial cell. E. coli cells containing the plasmid of interest are first harvested from the fermentation medium to provide a cell paste or slurry. Any conventional means to harvest cells from a liquid medium is suitable, including but not limited to centrifugation or microfiltration. Subsequent purification typically involves a number of steps involving varying techniques such as filtration, precipitation, cesium chloride/ethidium bromide density gradients; and various forms of chromatography including ion/anion exchange, gel permeation, and reverse phase chromatography. Typically, several of these techniques will be employed in a series of steps to successively increase the purity of the plasmid DNA.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying figures, it is to be understood that the invention is not limited to those precise embodiments, and that various changes and modifications may be effected therein by one skilled in the art without departing from the scope or spirit of the invention as defined in the appended claims.

The following examples are provided to illustrate the present invention without, however, limiting the same hereto.

Example 1

Identification and Evaluation of Two Distinct Phenotypes of *E. coli* DH5

Chemicals—All chemicals are of reagent grade and purchased from either the Sigma Chemical Co. (St. Louis, Mo.) or Fisher Scientific Products (Springfield, N.J.). API20E test strips were purchased from bioMerieux (Canada).

Cultivation Media—DM-P5 chemically-defined medium contains the following ingredients: 7.0 g/L $KH_2PO_4$, 7.0 g/L $K_2HPO_4$, 6.0 g/L $(NH_4)_2SO_4$, 5.0 g/L L-Glutamic Acid, 10 g/L glycerol, 0.5 g/L NaCl, and sodium hydroxide to bring the pH to 7.2. The medium was sterilized 30 min in the autoclave, liquid cycle. When cool, a 1:1000 dilution of a trace element mixture is added which consisted of the following trace elements dissolved in 10% HCl and filter sterilized: 27 g/L Ferric Chloride ($FeCl_3.6H_2O$), 2.0 g/L Zinc Chloride ($ZnCl_2.4H_2O$), 2.0 g/L Cobalt Chloride ($CoCl_2.6H_2O$), 2.0 g/L Sodium Molybdate ($Na_2MoO_4.2H_2O$), 1.0 g/L Calcium Chloride ($CaCl_2.2H_2O$), 1.27 g/L Copper Chloride ($CuCl_2.2H_2O$), and 0.5 g/L Boric Acid ($H_3BO_3$). This DM-P5/trace element mixture is stored at 4° C. When the medium is used, a 1:120 dilution of the following Th/Mg/Neo solution is added: 24 g/L thiamine hydrochloride, 240 g/L $MgSO_4.7H_2O$, and 9.6 g/L neomycin sulfate. Difco Bacto Agar, 15 g/L, was added to the above medium to prepare agar plates. Columbia 5% sheep's blood agar (SBA) plates, Trypticase soy agar plates (TSA), and Levine EMB and LES Endo agar plates were purchased from Fisher Scientific.

Culture Purity Assay—Fermentor broth samples were streaked onto TSA and blood agar plates and incubated at 25° C. and 35° C. Plates were examined after 48 hours and 7 days for culture purity.

Results—The initial observation of two distinct phenotypes of *E. coli* DH5 cells occurred during production of clinical material to support safety assessment studies for two potential Influenza DNA vaccines, Influenza NP and M1. The final fermentor broth samples for the GMP fermentations exhibited two distinct colony morphologies on blood agar when tested for routine culture purity. The dominant phenotype was gray in color and appeared as an irregular shaped, flat and translucent colony. The minor phenotype was white in color and appeared as a smooth, raised and circular colony. The minor, white colonies were identical in morphology to the *E. coli* DH5 cloning host strain initially used. It was later determined that the two cellular phenotypes were present in the Pre-Master, Master and Working Cell Banks used for the fermentations (Table 1).

TABLE 1

Population of white and gray phenotypic colonies in Cell Bank and fermentation broth for Influenza NP and M1 constructs.

| Sample plated | % white phenotype | % gray phenotype |
|---|---|---|
| M1 Source Material for Cell Bank | not tested | not tested |
| M1 Pre-Master Seed | 100% | 0% |
| M1 Master Seed | 1% | 99% |
| M1 Working Seed | 2.5% | 97.5% |
| M1 F38904 GMP Fermentation | 1.5% | 98.5% |
| NP Source Material for Cell Bank | 100% | 0% |
| NP Pre-Master Seed | 100% | 0% |
| NP Master Seed | 86% | 14% |
| NP Working Seed | 1% | 99% |
| NP F38951 GMP Fermentation | 1% | 99% |

The presence of both phenotypes went undetected on the chemically-defined agar (DM-P5) used to maintain the cultures since both colony types appear identical when incubated for 48 hours at 37° C. on this agar. Therefore, isolated colonies for each phenotype were obtained by duplicate streaking onto blood agar and DM-P5 agar plates. A pure gray colony was isolated from the chemically-defined agar (DM-P5) plate when the corresponding blood agar plate contained a uniform population of gray-colored colonies.

To further examine the gray and white clonal isolates, isolated colonies were streaked onto DM-P5 agar plates containing neomycin (the plasmid vector in these cultures contains the neomycin resistance marker), DM-P5 agar plates lacking neomycin, and *E. coli* differential agars (LES Endo and Levine EMB agars). Cells containing the plasmid can grow on both DM-P5 plates, with or without neomycin. LES Endo and Levine EMB agars are selective agars used to distinguish and identify gram negative Enterobacteriaceae and *E. coli*. Approximately 50 colonies isolated from the GMP fermentations and Working Cell Banks were evaluated on the above agars. All of the clonal isolates grew on DM-P5 plates supplemented with neomycin, suggesting that they contained the plasmid conferring resistance. The presence of the plasmid in both phenotypes was confirmed by agarose gel electrophoresis for the Influenza NP and M1 constructs. Growth of these clonal isolates on the differential agar plates was typical for *E. coli*. The excellent *E. coli* profile match by API20E analysis further confirmed that the gray and white clones were indeed *E. coli*. FAME (fatty acid methyl ester) analysis performed on representative colonies to determine the relatedness of the two types of colonies indicated that the clonal isolates were identical to each other and to the DH5 cloning host strain, regardless of their phenotype on blood agar. The above results were strong evidence that the gray and white colonies were not different organisms but phenotypic variants of *E. coli* DH5.

A screening assay was developed to distinguish between the two colony morphologies using visual examination. A mixture of Influenza M1 white and gray clonal isolates were serially diluted, plated onto 5% Columbia Sheep's blood agar plates and incubated at 30° C., 37° C. or 42° C. for specified periods of time. The optimum condition for phenotype differentiation was an incubation period of 48 hours at 30° C. This blood agar phenotype screening assay was used for all future plating experiments and also served as an important tool for the screening of high producers for later constructs under development.

Example 2

E. coli DH5 Gray Phenotype Enrichment Study

Influenza M1 Gray Phenotype Enrichment Study—Separate cultures of white and gray phenotypic colonies containing the Influenza M1 DNA plasmid vector were grown in DM-P5 chemically-defined medium to exponential phase. The cultures were then mixed in equal proportions and used to inoculate a fresh flask of DM-P5 medium. The starting $OD_{600}$ for each enrichment flask was 0.001. The mixed culture was grown for 17 generations and then inoculated into a second enrichment flask. This ensured that the cells were in exponential growth at each transfer step. This process was repeated for a total of four enrichments. An aliquot of cells was frozen in 40% glycerol (v/v) from each enrichment step and analyzed by the blood agar phenotype screening assay described in Example 1 to determine the percentage of gray phenotypic colonies after enrichment.

HIV-Gag Gray Phenotype Enrichment Study—A kinetic enrichment experiment was set up using a construct that harbored the HIV-Gag gene. Pure cultures of HIV-Gag white colonies and HIV-Gag gray colonies were mixed at the following ratios: 100% gray, 5% gray, 20% gray, 50% gray, 70% gray and 0% gray. Each flask was grown for 17 generations in DM-P5 chemically-defined medium and similarly transferred five times as described in the Influenza M1 Gray Phenotype Enrichment Study. After each enrichment, an aliquot of cells was removed and frozen in 40% glycerol (v/v). At the end of the experiment, these samples were serially diluted and analyzed by the blood agar phenotype screening assay described in Example 1 to enumerate the population of gray phenotypic colonies after enrichment.

Results—Two separate experiments were performed to investigate the observation that the gray phenotypic E. coli DH5 colonies were enriched during growth in DM-P5 chemically-defined medium. Both Influenza M1 and HIV-Gag constructs were used to determine if the enrichment phenomenon was construct specific.

Figure 1:
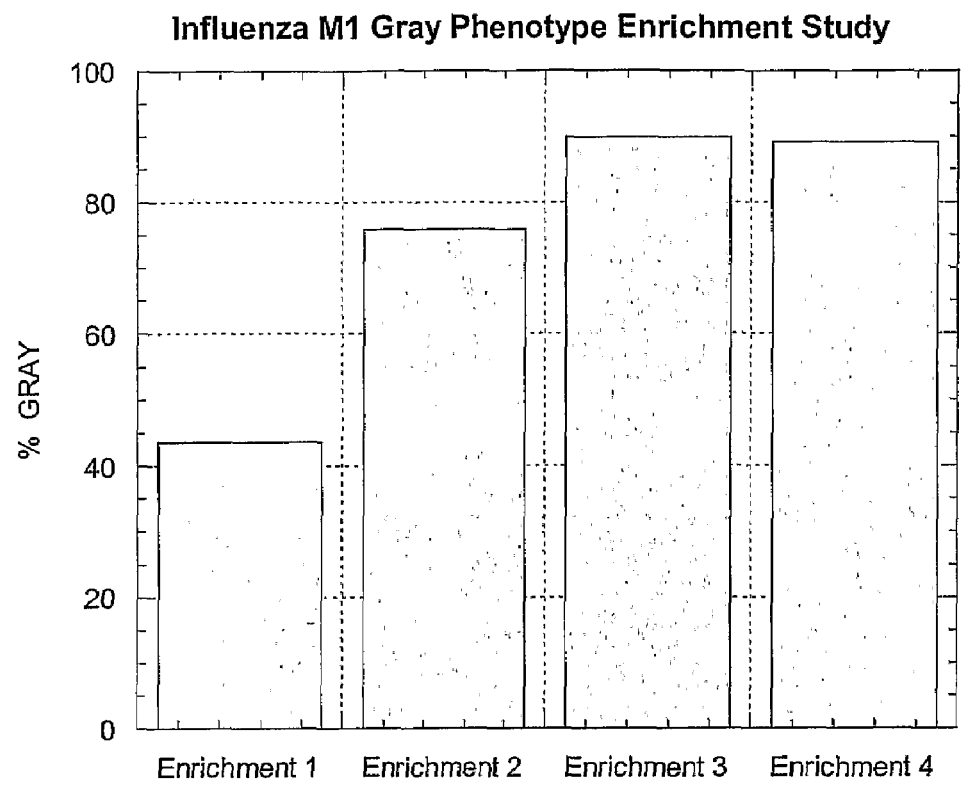

The Influenza M1 gray phenotype enrichment study demonstrated that the gray phenotypic colonies have a selective growth advantage over the white colonies under the growth conditions tested. The percentage of Influenza M1 gray colonies increased from 44% to 89% over the course of four enrichments in DM-P5 medium (FIG. 1).

To further examine this observation, a kinetic enrichment experiment was performed using an HIV-Gag construct. Varying ratios of white:gray HIV-Gag phenotypic colonies were used to inoculate DM-P5 medium. Each test flask went through a total of five enrichments. After the third enrichment (51 generations), the resulting cell populations consisted of greater than 95% of gray phenotypic colonies in all of the test flasks (FIG. 2). Furthermore, the flasks initially having 100% of gray colonies did not show any reversion to the white phenotype; while the flasks starting with 100% of white colonies did show a 2-10% increase of gray phenotypic colonies through the fifth enrichment.

Based on these findings, kinetic growth studies were conducted on white and gray isolated cultures obtained from four separate E. coli constructs (Influenza M1 and NP, Herpes Simplex Virus gD, and HIV-Gag). Pure cultures of gray and white phenotypic colonies for each construct were grown separately in DM-P5 medium, and a growth curve for each culture was obtained during exponential growth to determine their specific growth rates (Table 2). In all instances, the gray phenotype exhibited a slight growth rate advantage ($\Delta\mu=0.01$-$0.06$) over the white phenotype, supporting earlier findings of enrichment of gray phenotypic colonies in a heterogeneous gray/white population.

TABLE 2

Specific growth rates (μ) for gray and white phenotypic colonies isolated from DNA vaccine cultures.

| | M1 white | M1 gray | NP white | NP gray | gD white | gD gray | HIV white | HIV gray |
|---|---|---|---|---|---|---|---|---|
| μ | 0.44 | 0.47 | 0.45 | 0.46 | 0.39 | 0.44 | 0.40 | 0.46 |
| Δμ (gray – white) | 0.03 | | 0.01 | | 0.05 | | 0.06 | |

Example 3

Correlation of Plasmid DNA Concentration to Gray Phenotypic Colonies of E. coli DH5

Transformation—Two methods were used to transform E. coli DH5 cells to obtain clonal isolates to be screened for plasmid productivity. For the first method, 100 ng (2 μL) of plasmid DNA was added to 100 μL of E. coli DH5 competent cells. Competent cells were prepared using standard molecular biology practices. This mixture was stored on ice for 30 minutes and then subjected to heat treatment at 42° C. for 90 seconds. These tubes were chilled on ice and then 800 μL of DM-P5 medium was added to each tube. These tubes were then incubated at 37° C. for 90 minutes for recovery of antibiotic resistance. The recovered culture was then spread plated onto DM-P5 agar plates and incubated for 36 hours to obtain transformants. The second method of transformation used electro-transformation and the Bio-Rad Pulser (Hercules, Calif.) system. For this procedure, 80 μL of competent cells was mixed with 0.5-4.0 μg of plasmid DNA. This mixture was transferred to a cold electroporation cuvette and pulsed once at a setting of 1.8 kV. To this cuvette, 1.0 mL of DM-P5 medium was added. This suspension was transferred to a sterile 15 mL centrifuge tube and incubated at 37° C. for 3 hours to recover antibiotic resistance. After the recovery period, the suspension was plated onto, or diluted into, DM-P5 media and incubated at 37° C. to obtain transformants.

23 Liter Fermentation—A 23 L bioreactor containing 15 L of DM-P5 chemically-defined media was inoculated with 0.1% (v/v) of a thawed seed suspension. The bioreactor was operated with a 150 rpm agitation (minimum set point) and a 0.3 bar backpressure and sparged with air at a rate of 7.5 L/m. The dissolved oxygen tension was maintained at 30% by computer controlled ramping of the agitation. The pH was controlled at 7.2. When the $OD_{600}$ was between 8 and 10, the airflow and backpressure were increased to 12 L/m and 1 bar, respectively, and a solution consisting of 50% glycerol (v/v): 25% L-glutamic acid (w/v) was fed at a rate of 3.2 mL/L/min. The fermentation was run for 50 hours. Specific productivity was determined using cell lysis and HPLC anion exchange methods.

DME-B12 Cultivation Medium—DME-B12 medium is based on DM-P5 medium. DME-B12 medium consists of the following ingredients: 7.0 g/L $KH_2PO_4$, 14.0 g/L $K_2HPO_4$, 3.0 g/L $(NH_4)_2SO_4$, 0.5 g/L NaCl and 2 ml/L Glycerol. The pH was adjusted to 7.2 with 50% NaOH, and then sterilized 30 min in the autoclave, liquid cycle. When cool, a 1:1000 dilution of a trace element mixture was added which consisted of the following trace elements dissolved in 10% HCl and filter sterilized: 27 g/L Ferric Chloride ($FeCl_3 \cdot 6H_2O$), 2.0 g/L Zinc Chloride (ZnCl$_2$.4H$_2$0), 2.0 g/L Cobalt Chloride (CoCl$_2$.6H$_2$0), 2.0 g/L Sodium Molybdate (Na$_2$MoO$_4$.2H$_2$0), 1.0 g/L Calcium Chloride (CaCl$_2$.2H$_2$0), 1.27 g/L Copper Chloride (CuCl$_2$.2H$_2$0), and 0.5 g/L Boric Acid (H$_3$BO$_3$). This DME-B12/trace element mixture is stored at 4° C. When the medium is used, a 1:120 dilution of the following Th/Mg/Neo solution is added: 24 g/L thiamine hydrochloride, 240 g/L MgSO$_4$.7H$_2$0, and 9.6 g/L neomycin sulfate.

Shake Flask Fermentation (SFF)—This method is a scaled down version of the 23-L fermentation process described above and uses a 250 mL test flask setup. The flasks were designed with holes in their caps for feed delivery. Test cultures were grown to exponential phase (OD$_{600}$=1.5-2.5) in DME-B12 medium. Once cultures reached this stage, a solution consisting of 4.6% glycerol (v/v) and 2.9% L-glutamic acid (w/v) was fed at a rate of 6.4 µL/h/mL broth. A Watson Marlow 205U pump (Wilmington, Mass.) was used to deliver the feed solution. The flasks were incubated at 37° C. for 40 hours with constant agitation at 220 rpm. Specific productivity was determined using cell lysis and HPLC anion exchange methods.

Cell Lysis Procedure—23 L fermentation or SFF OD$_{600}$ samples were measured, and an OD10 pellet was made (10/OD of culture=µl of sample centrifuged at 14,000 rpm, 5 min) The supernatant was removed, and the pellet was lysed as follows using standard molecular biology reagents. The pellet was first resuspended in 0.5 mL of STET buffer (8% sucrose, 5% Triton X-100, 50 mM EDTA, 50 mM Trizma base), and 0.5 mL of a lysozyme solution (4 mg/mL) was then added. The tubes were vortexed to resuspend the cells. The tubes were then incubated for 45 min at 37° C. and placed in a boiling water bath for 1 min. After boiling, the tubes were centrifuged for 15 min at 14,000 rpm. The supernatant was then poured into labeled HPLC vials to which 10 µL of RNASE was added. The supernatant was then analyzed by anion exchange chromatography to quantitate the amount of supercoiled plasmid DNA.

Anion Exchange HPLC—The separation of supercoiled and relaxed plasmid DNA from lysed fermentation samples was achieved employing a Waters HPLC system (Milford, Mass.) comprised of three pumps, a UV detector, an autoinjector and a PC computer system. A GEN-PAK FAX anion exchange column (4.6×100 mm) (Waters Corporation) was used. Separation was obtained by using a gradient of 1 M NaCl in 25 mM Tris-HCl, 1 mM EDTA, pH 8 (Buffer B). Buffer A was identical to Buffer B minus NaCl. A 0.04 M phosphoric acid solution (Buffer C) was used to wash the column between injections. A constant flow rate of 0.75 mL/min was used. The initial gradient of 35/65 (v/v) A:B, 3 minutes, was increased to 25/75 (v/v) A:B over 30 minutes. The column was then washed for 6 min with Buffer C, followed by 10 min of Buffer B. The system was re-equilibrated back to 70/30 (v/v) A:B for 13 min before performing the next injection. Detection at 260 nm indicated that supercoiled plasmid DNA eluted after 10 min and relaxed, open-circle plasmid DNA eluted after 9.5 min. Specific productivity of supercoiled plasmid DNA was reported as µg plasmid DNA/mL OD2 pellet or µg plasmid DNA/mg DCW (dry cell weight).

Results—The data obtained from the plating experiments for the Influenza NP and M1 Cell Bank cultures and GMP fermentation samples, summarized in Table 1 and FIG. 1, suggested a correlation between high plasmid productivity and the gray phenotypic colonies identified herein. GMP fermentations of Influenza M1 and NP yielded supercoiled plasmid DNA titers of 36 µg/mg DCW and 31 µg/mg DCW, respectively. In all cases, the broth consisted of 99% gray phenotypic colonies. The plasmid copy number was determined from cell lysates for Influenza M1 and NP white and gray isolates, confirming that microbial cells isolated from gray phenotypic colonies contain a higher plasmid copy number than cells isolated from white phenotypic colonies.

It was apparent from the work done with the Influenza constructs that high levels of plasmid DNA can be produced when selecting for gray phenotypic colonies after transformation. Several other constructs showed a similar correlation between gray phenotypic colonies and high plasmid yield (Table 3). For one construct in particular, HSV-gD, productivity was increased from <1 µg/mL to 20 µg/mL OD2 pellet of supercoiled plasmid DNA. This was achieved by isolating gray phenotypic colonies from a mixed culture consisting of only 14% of the gray phenotype. From this mixture, three separate gray clonal isolates were tested in a shake flask fermentation system or a 23-L bioreactor. Each produced ≧15 µg/mL OD2 pellet of supercoiled DNA.

TABLE 3

Productivity data for white and gray clonal isolates

| Isolate Fermented at the 23 L or SFF Scale | Supercoiled Plasmid DNA Produced (µg/mL/OD2 pellet) |
|---|---|
| HSV-gDm.7 mixed culture (86% white/14% gray) | <1 |
| HSV-gDm.7 - gray isolate N-11A | 15 |
| HSV-gDm.7 - gray isolate N-19A | 23 |
| HSV-gDm.7 - gray isolate N5-1A | 20 |
| Influenza M1 white isolate | <1 |
| Influenza M1 gray isolate | 23 |
| Influenza NP white isolate | 7 |
| Influenza NP gray isolate | 19 |
| HSV-ΔgB white isolate | <1 |
| HSV-ΔgB gray isolate | 20 |
| HIV-Gag white isolate | <3 |
| HIV-Gag gray isolate | 22 |

Example 4

Selection Strategies to Enrich for Gray Phenotypic Colonies of *E. coli* DH5

Two strategies were developed to select and enrich for gray phenotypic colonies of *E. coli* DH5 after transformation. The first of these strategies relied on the fact that gray phenotypic colonies demonstrate a higher specific growth rate than white phenotypic colonies. Thus, the gray colonies will out compete the white phenotype over successive enrichments. For this protocol, transformed and recovered cells were enriched in DM-P5 chemically-defined media, with subsequent plating onto blood agar and DM-P5 agar plates. Individual colonies were picked from the DM-P5 plates based on the percentage of the gray phenotypic colonies detected on their corresponding blood agar plates. This strategy was used to identify high plasmid DNA clonal isolates for three plasmids encoding viral proteins, HSV-gB, HIV-Gag and HIV-env. During these enrichments, the percentage of gray phenotypic cells always leveled off between 5-15% of the total cell population in the enrichment flasks.

While developing a second strategy for isolating high producing, gray clonal isolates, it was observed that the initial transformed, recovered cell population displayed two distinct phenotypes when plated onto DM-P5 chemically-defined agar plates and incubated for 5 days at 37° C. Both cream-colored and cream-colored colonies with a brown bulls-eye center were detected. Cream-colored colonies gave rise to the desired high producing gray phenotypic colonies, while cream-colored colonies with brown centers did not. This was demonstrated with HSV-gD. Gray clonal isolates of HSV-gD, N-11A, N-19A and N5-1A (Table 3), all produced cream-colored colonies on DM-P5 chemically-defined agar and gray colonies on blood agar. These clonal isolates also demonstrated high titers of supercoiled plasmid DNA. No isolate forming cream-colored colonies with brown centers on DM-P5 chemically-defined agar were able to produce high plasmid DNA titers or give rise to the gray phenotype. However, a single colony exhibiting the cream-colored morphology on DM-P5 agar that is picked and expanded in liquid DM-P5 media can give rise to a mixed population consisting of both white and gray phenotypes. Therefore, cream-colored colonies obtained on DM-P5 chemically-defined agar plates after transformation are pre-disposed to produce the gray phenotype. This indicates that the gray phenotype evolves from a single colony during the post-transformation selective enrichment period. Although not every cream-colored isolate will yield a gray phenotype, these are the only colony types from which the gray phenotype has evolved. Therefore, it is important to select for gray phenotypic colonies by duplicate plating on blood agar and DM-P5 chemically-defined agar plates to ensure that a high-producing clonal isolate is selected.

Example 5

Improved Protocol for Master Cell Bank Production

Using the improved selection and enrichment techniques described above, high producing isolates were obtained that were used as the seed cultures to produce the Pre-Master, Master and Working Seed stock cultures for three DNA vaccine constructs, HSV-ΔgB, HSV-gD and HIV-Gag. When comparing the blood agar plating results for the Pre-Master, Master and Working Cell Bank cultures produced for these constructs with earlier results obtained for the Influenza M1 and NP constructs (Table 1), the phenotypic diversity originally present in the Master Cell Bank cultures was eliminated and high plasmid producing strains were obtained (Table 4). This was extremely critical to the clinical material produced from these constructs since a heterogeneous $E.$ $coli$ population could have an impact on the consistency and yield of the fermentation process. The Working Cell Bank cultures for the HIV-Gag construct were later used for GMP fermentation to produce the cell paste for clinical studies. No cultural heterogeneity was detected in this fermentation process. The gray phenotype also did not show any reversion to the white phenotype during enrichment studies (FIG. 2), indicating the stability of this phenotype.

TABLE 4

Summary of Cell Bank plating results for the HSV-ΔgB, HSV-gD and HIV-Gag constructs.

| Sample plated | % gray phenotype | Specific productivity (µg plasmid DNA/mL OD2 pellet) |
|---|---|---|
| HSV-ΔgB Pre-Master Seed | >99% | not tested |
| HSV-ΔgB Master Seed | >99% | 22 |
| HSV-ΔgB Working Seed | >99% | 17 |
| HSV-gD Pre-Master Seed | >99% | not tested |
| HSV-gD Master Seed | >99% | 19 |
| HSV-gD Working Seed | >99% | 22 |

TABLE 4-continued

Summary of Cell Bank plating results for the HSV-ΔgB, HSV-gD and HIV-Gag constructs.

| Sample plated | % gray phenotype | Specific productivity (µg plasmid DNA/mL OD2 pellet) |
|---|---|---|
| HIV-Gag Pre-Master Seed | >99% | not tested |
| HIV-Gag Master Seed | >99% | 20 |
| HIV-Gag Working Seed | >99% | 23 |

Example 6

Preparation of Seed Stocks for the Production of Plasmid DNA by Cultivation of $E.$ $coli$ DH5

An aliquot of frozen cells of a high plasmid producing strain of $E.$ $coli$ DH5 selected for as per the process described above and harboring the V1Jns HIV Flgag plasmid, contained in a source vial, was used to inoculate three 2-L baffled shake flasks (each flask received 200 µL) containing 200 mL of medium A (Table 5). The flasks were incubated at 37±0.5° C. with shaking (@ 180-rpm on an orbital shaker with a 50 mm shaking diameter). Two of the flasks were used for monitoring purposes and the third flask was used to prepare the frozen cell suspension. When the optical density ($OD_{600}$) of the culture of the monitoring flasks reached a value in the range of 5 to 9, the optical density of the source flask was then checked to ensure that it had also reached a similar value. The source flask was then chilled on wet ice. An equal volume of chilled 40% glycerol solution in water (v/v) was added to the contents of the flask. The mixed suspension was dispensed (~1 mL) in cryovials that were immediately flash frozen on dry ice and stored at −65° C. This first seed stock was labeled "pre-master." A frozen suspension from a pre-master vial was thawed and used to prepare the master seed stock according to the protocol described above. A frozen suspension from a master vial was thawed and used to prepare the working seed stock according to the same protocol.

TABLE 5

Defined Culture Medium A.

| Components | Concentration |
|---|---|
| $KH_2PO_4$* | 7.0 g/L |
| $K_2HPO_4$* | 7.0 g/L |
| $(NH_4)_2SO_4$* | 6.0 g/L |
| Monosodium glutamate* | 5.0 g/L |
| Glycerol* | 10.0 g/L |
| Thiamine Hydrochloride[1] | 0.20 g/L |
| $MgSO_4 \cdot 7H_2O$[1] | 2.0 g/L |
| Neomycin Sulfate[1] | 0.08 g/L |
| Trace Elements[2] | 1.0 mL/L |

*These components form the basal medium. They are dissolved in water and the pH is adjusted to 7.2 with 50% NaOH. The basal medium is sterilized by filtration through a 0.22 µm membrane.
[1]A stock solution was prepared on the day of use by dissolving Thiamine-HCl (24 g/L), $MgSO_4 \cdot 7H_2O$ (240 g/L) and Neomycin Sulfate (9.6 g/L) in deionized water and filter sterilizing it (0.22 µm membrane). An amount of 8.3 mL/L of this stock solution is added per liter of medium to yield the desired final concentrations.
[2]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). The solution is filtered sterilized through a 0.22 µm membrane.

Example 7

Preparation of Large Seed Stocks for the Production of Plasmid DNA by Cultivation of $E.$ $coli$ DH5

A laboratory supply of frozen cells of a high plasmid producing strain of $E.$ $coli$ DH5 selected for as per the process described herein and harboring the V1Jns HIV Flgag plasmid inoculum was prepared by filling two 250-mL baffled Erlenmeyer flasks with 30 mL of medium A (Table 5). Each flask was inoculated by pipetting 30 µL of thawed GMP HIV-FL-gag master seed from a 4-mL vial into each flask. The flasks were incubated at 37±0.5° C. with shaking at 220-rpm on an orbital shaker (Adolf Kühner AG; Birsfelden, Switzerland) with a 50 mm shaking diameter. One flask was available for monitoring, while the second served as the inoculum source for the bioreactor. When the optical density at 600 nm ($OD_{600}$) of the culture in the monitoring flask achieved a value in the range of 5 to 9 (approximately 26 hours post-inoculation), the $OD_{600}$ of the source flask was measured to ensure it had attained a similar value.

A 30-L bioreactor (B. Braun Biotech, Inc.; Allentown, Pa.), interfaced with a SCADA control system utilizing Gas Works software (Thermo ONIX Corp.), was sterilized in situ containing 15 L of medium B (Table 6). The prepared bioreactor was inoculated with 15 mL (0.1% v/v) of the fresh shake-flask culture prepared as described above by injecting the inoculum through a sterilized septum in a bioreactor port with a 20-mL syringe fitted with an 18-gauge needle. The cultivation conditions were: temperature, 37° C.; back-pressure, 4.5 PSI; airflow, 7.5 slpm. The dissolved oxygen level (DO), carbon evolution rate (CER), oxygen uptake rate (OUR) (Prima V Mass Spectrometer Model 600, Thermo ONIX Corp., Houston, Tex.), cell density (OD probe, Monitek, Bedford, Mass.) and pH were simultaneously measured and recorded on-line. The DO was maintained to a set-point (greater or equal to 30% of air saturation) by automatic-feedback cascade control of the agitation speed (between 250 and 750 rpm). The culture pH was maintained to 7.1±0.1 by automatic addition of a sterile 30% NaOH Solution. Once mid-log phase growth was attained, indicated by an on-line measurement of the CER equal to 35 mmol/L/hr, a 5-L volume of the culture was aseptically transferred into a sterile 10-L plastic carboy containing 5 L of a 50% glycerol solution. The carboy was placed on a magnetic stirring plate in a biologics safety cabinet and the contents were continuously mixed to provide even suspension of the cells throughout the filling procedure. Via a peristaltic pump and sterilized silicon tubing, 500-mL bottles (Nalgene) were filled with 300 mL of the working seed. The filled bottles were initially cooled by covering with dry-ice and then were transferred to a −65° C. freezer for storage.

TABLE 6

Defined Culture Medium B.

| Components | Concentration |
|---|---|
| [1]$KH_2PO_4$ | 7.0 g/L |
| [1]$K_2HPO_4$ | 7.0 g/L |
| [1]$(NH_4)_2SO_4$ | 6.0 g/L |
| [1]Monosodium glutamate | 5.0 g/L |
| [1]Glycerol | 10.0 g/L |
| [1]Ucon | 0.3 mL/L |
| [2]Thiamine Hydrochloride | 0.20 g/L |
| [2]$MgSO_4 \cdot 7H_2O$ | 2.0 g/L |
| [2]Neomycin Sulfate | 0.08 g/L |
| [3]Trace Elements | 1.0 mL/L |

[1]The ingredients were added to 15 L of water, and the fermentor was steam sterilized in place at 123° C. for 25 min.
[2]A concentrated solution (thiamine: 24 g/L; $MgSO_4 \cdot 7H_2O$: 240 g/L; neomycin sulfate 9.6 g/L) is prepared and filtered sterilized into the seed fermentor to yield the desired final concentration.
[3]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). The trace element solution was added post sterilization.
The pH of the medium was adjusted to 7.1 prior to inoculation.

Example 8

Analytical Procedures for Plasmid Quantification

Cell Lysis—Cells from each sample were prepared for lysis by calculating the culture volume that would be required to obtain an OD of 10 in 1 mL final volume, with subsequent centrifugation of the culture in an Eppendorf Centrifuge 5415 C (Westbury, N.Y.) for five min at 14,000 rpm. The supernatant was discarded and the pellets were stored in a −70° C. freezer until the time of lysis. Upon thawing, each pellet was resuspended in 500 µL of STET Buffer (per L distilled $H_2O$): Tris-EDTA Buffer (Sigma), 50 mL; 0.5 M EDTA pH 8 (Sigma), 190 mL; sucrose, 80 g; Triton X-100 (Sigma), 20 g; followed by 500 µL of Lysozyme Solution (per L STET buffer: lysozyme (Sigma), 0.4 g). The tubes were incubated at 37° C. for 45 min in an Eppendorf Thermomixer R (Westbury, N.Y.), shaking continuously at 500 rpm. After incubation, the tubes were inserted into a floating rack and set in boiling water for one minute. The cell debris was separated by centrifugation in an Eppendorf Centrifuge 5415 C for 15 min at 14,000 rpm. The supernatant of each tube was transferred into a 1.8 mL HPLC vial, along with 10 µL of RNAce-It! Ribonuclease Cocktail (Stratagene, La Jolla, Calif.). The vials were each capped and gently shaken to mix the contents.

HPLC Assay—Plasmid DNA was quantified by use of a HPLC system (Gilson, Middleton, Wis.) equipped with a Waters Gen-Pak FAX column (4.6×100 mm) (Milford, Mass.). Separation of the supercoiled plasmid DNA was achieved with a gradient-based elution of a mobile phase consisting of Buffer A and Buffer B delivered at a rate of 0.75 mL/min. The concentration of Buffer A [per 973 mL HPLC-Grade $H_2O$: 1 M Tris-HCl pH 8.0, 25 mL; 0.5 M EDTA pH 8.0, 2 mL] decreased from 70% to 35% over the first two minutes of the assay, while the concentration of Buffer B [per 773 mL HPLC-Grade $H_2O$: 1 M Tris-HCl pH 8.0, 25 mL; 0.5 M EDTA pH 8.0, 2 mL; 5 M NaCl, 200 mL] increased from 30% to 65%. At this point, the sample was injected and the mobile phase continued at 35% Buffer A and 65% Buffer B for seven minutes while the sample components eluted. The mobile phase switched to 100% Buffer C [per L HPLC-Grade $H_2O$: 85% $H_3PO_4$ HPLC-Grade, 4.61 mL] for 12 minutes for cleaning, at which point the mobile phase returned to 70% Buffer A and 30% Buffer B. Detection was performed at 260 nm at 25° C. Under these conditions, supercoiled DNA eluted after approximately 5 minutes. Supercoiled plasmid DNA concentrations were calculated against a standard curve generated using pure plasmid DNA. The specific and volumetric plasmid yields were calculated by the automatic integration of the supercoiled DNA peak, including the volume of cell culture needed to prepare the $OD_{10}$ pellet and the dry cell weight measurement (DCW).

Example 9

Plasmid Production Methods

Plasmid Production Method 1—A 20-L seed fermentor was prepared to contain approximately 12.7 kg of sterile, chemically defined medium C (Table 7). Two frozen working seed vials of E. coli DH5 strain harboring the V1Jns HIV Flgag plasmid, prepared as described in Example 6, were thawed at ambient temperature, and 6 mL of the cell suspension were added to 200 mL of saline phosphate buffer (per L of water; NaCl: 7.0 g, $KH_2PO_4$: 0.2 g, $K_2H_2PO_4$: 0.674 g). The entire volume was pumped into the 20-L seed fermentor. Initial fermentation conditions were as follows: temperature, 37° C.; airflow, 2 L/min; agitation, 100 rpm; and pressure, 0.5 bar. The initial value of the pH was in the 7.0-7.1 range. No pH control was used during the inoculum production. When the initial dissolved oxygen level decreased from 100% to 50%, at about 8-12 hours post inoculation, the airflow set point was manually increased to 6 L/min. As demand increased, dissolved oxygen level was maintained at a set point greater or equal to 30% throughout the remainder of the fermentation cycle by automatic ramping of the agitation speed within the range of 100-800 rpm. Dissolved oxygen level, CER, Oxygen Uptake Rate (OUR), pH, and cell density of the fermentation broth (using a Monitek OD probe and transmitter) were all measured on-line. After about 17-20 hours post inoculation the cells reached mid-log phase as indicated by on-line measurements of both CER and culture density which reach about 35-50 mMoles/L/h and 0.80-1.0 absorbance units (equivalent to an off-line OD @ 600 nm between 8-10), respectively. At that time, using a transfer bottle, 600 mL of the seed culture were aseptically transferred from the seed fermentor to the 1000-L production fermentor.

Figure 5:
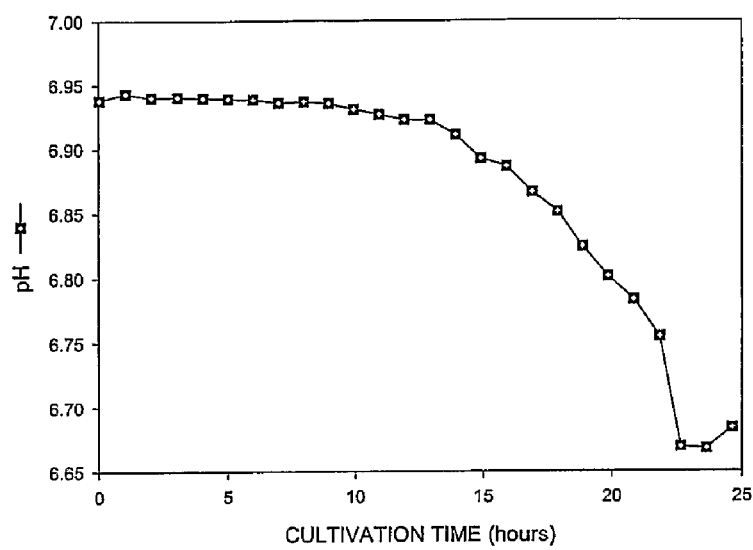
FIG. 5 summarizes the pH data for a typical seed fermentor, as demonstrated by a seed fermentor used to cultivate cells containing the V1Jns-gag plasmid according to Plasmid Production Method 1 of Example 9.

FIGS. 3-5 summarize the key data gathered for a typical seed fermentor used to produce cells containing the V1Jns gag plasmid. FIG. 3, panels A and B, clearly shows that aerobic cultivation was maintained at all time, as demonstrated by the dissolved oxygen value being above 30% saturation as a result of controlling both the air flow and agitation rate. The kinetics of the metabolic activity measurements, CER and OUR (FIG. 4, panel A), and on-line optical density monitoring (FIG. 4, panel B) clearly indicate that the cells were actively growing without limitation when they were transferred to the production fermentor. Finally, data presented in FIG. 5 show that pH value declined during active growth to reach a final value of about 6.70-6.65.

A 1000-L production fermentor was batched with approximately 600 L of sterile, chemically defined medium D (Table 8). Initial fermentation conditions were as follows: temperature, 37° C.; airflow, 200 L/min; agitation, 100 rpm; and pressure, 7.5 PSI. Dissolved oxygen level was maintained to a set point greater or equal to 30% of air saturation ambient pressure. The pH of the culture was maintained within the range of 7.0 to 7.2 by automatic addition of 25% (v/v) phosphoric acid or 30% (v/v) sodium hydroxide throughout the fermentation cycle. Dissolved oxygen level, CER, OUR, cell density (using on-line Monitek probe), and pH of the fermentation broth were all measured on-line. At about 15 hours after inoculation, when on-line measurements for CER read about 35-40 mMoles/L/h and for culture density read about 0.70-0.80 absorbance units (equivalent to an off-line OD @ 600 nm between 8-10), feeding of a solution containing 50% glycerol and 25% monosodium glutamate was initiated. To accommodate the high dissolved oxygen demand and in order to maintain the DO>30%, the vessel pressure and the airflow were both manually increased to 15 PSI and 600 L/min respectively (at the time of feeding initiation), while the agitation was automatically ramped via a computer feed-back loop. An amount, totaling approximately 75 L of feed solution was pumped over 35 hours (rates varying approximately between 2.66 to 3.66 g/L/h). The feeding was initiated at the lower set point and manually increased over a period of 2 hours to its high value once respiratory activity (measured by CER) has peaked.

FIGS. 6-9 summarize the key data collected for these fermentations. During the feeding process the cells were growing at a linear rate with the CER and OUR remaining approximately constant with values between 35 to 60 mM/L/h and 40 to 60 mM/L/h, respectively (FIG. 8, panels A and B). After about 50 hours of cultivation, the final culture density is about 1.5 absorbance on-line units, corresponding to an off-line density (OD @ 600 nm) of about 65 units. FIG. 6 (panels A and B) shows that, due to the combination of increasing back pressure, agitation rate (rpm) and air flow, the dissolved oxygen (%) remained at or greater than the 30% set point. During peak demand (ca. 20 hours into the process), the oxygen demand peaked at about 80 mM/L/h. Growth and metabolism of the cells were constantly monitored through on-line optical density and mass-spectrometry readings. FIG. 8 (panel A) shows that an exponential growth phase took place up to about 20 hours post inoculation (corresponding to peak OUR and CER (panel B)), followed by a more reduced growth achieved during the feeding phase of the process, where both respiratory activity and growth rate were directly dependent of the rate of nutrient feeding. The final specific and volumetric plasmid DNA productivities were 24.45 µg plasmid per mg of dry cell weight and 0.538 g/L, respectively.

TABLE 7

Defined Culture Medium C

| Components | Concentrations |
|---|---|
| [1]$KH_2PO_4$ | 7.0 g/L |
| [1]$K_2HPO_4$ | 7.0 g/L |
| [1]$(NH_4)_2SO_4$ | 6.0 g/L |
| [1]NaCl | 0.5 g/L |
| [2]Monosodium glutamate | 5.0 g/L |
| [2]Glycerol | 10.0 g/L |
| [3]Ucon | 0.3 mL/L |
| [4]Thiamine Hydrochloride | 0.20 g/L |
| [4]$MgSO_4 \cdot 7H_2O$ | 2.0 g/L |
| [4]Neomycin Sulfate | 0.08 g/L |
| [5]Trace Elements | 1.0 mL/L |

The seed fermentor is batched and sterilized with 8 kg of purified water.

[1]A 10X concentrated salts solution is prepared and the pH is adjusted to 7.2 with 50% NaOH. The concentrated basal salt solution is filtered sterilized into the seed fermentor to yield the desired final concentration.

[2]A concentrated solution (MSG: 250 g/L; glycerol: 500 g/L) is prepared and filtered sterilized into the seed fermentor to yield the desired final concentration.

[3]Ucon is prepared as a diluted solution (1.5%) in water, heat sterilized and aseptically transferred to the seed fermentor to yield the desired final concentration.

[4]A concentrated solution (thiamine: 24 g/L; $MgSO_4 \cdot 7H_2O$: 240 g/L; neomycin sulfate 9.6 g/L) is prepared and filtered sterilized into the seed fermentor to yield the desired final concentration.

[5]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). A diluted solution (12 mL in 200 mL of water) is prepared and filtered sterilized into the seed fermentor.

TABLE 8

Defined Culture Medium D.

| Components | Concentrations |
|---|---|
| [1]$KH_2PO_4$ | 7.0 g/L |
| [1]$K_2HPO_4$ | 7.0 g/L |
| [1]$(NH_4)_2SO_4$ | 6.0 g/L |
| [1]NaCl | 0.5 g/L |
| [2]Monosodium glutamate | 5.0 g/L |
| [2]Glycerol | 10.0 g/L |
| [3]Ucon | 0.3 mL/L |
| [4]Thiamine Hydrochloride | 0.20 g/L |

TABLE 8-continued

Defined Culture Medium D.

| Components | Concentrations |
|---|---|
| [4]$MgSO_4 \cdot 7H_2O$ | 2.0 g/L |
| [4]Neomycin Sulfate | 0.08 g/L |
| [5]Trace Elements | 1.0 mL/L |

The production fermentor is batched and sterilized with 525 kg of purified water.
[1]A 10X concentrated salts solution is prepared and the pH is adjusted to 7.2 with 50% NaOH. The concentrated basal salt solution is filtered sterilized into sterile carboys. The sterile 10X solution is then pumped into the fermentor through a sterile filtration apparatus. A total volume of 60 L of the 10X solution is used to yield the desired final concentration.
[2]A concentrated solution (MSG: 250 g/L; glycerol: 500 g/L) is prepared and filtered sterilized into carboys. The concentrated solution is pumped into the fermentor at the time of batching (12 L) to yield the desired concentrations. Carboys containing the same formulation solution are used for feeding purpose.
[3]Ucon is prepared as a diluted solution (60%) in water, heat sterilized and aseptically transferred to the seed fermentor to yield the desired final concentration.
[4]A concentrated solution (thiamine: 24 g/L; $MgSO_4 \cdot 7H_2O$: 240 g/L; neomycin sulfate: 9.6 g/L) is prepared and filtered sterilized into the seed fermentor to yield the desired final concentrations.
[5]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). The solution (600 mL) is filtered sterilized into the production fermentor. After the additions, the weight of the fermentor is brought up to 600 kg by addition of purified water through a sterile filtration apparatus. pH of the fermentation is controlled by addition of sterile NaOH (30% in water) or phosphoric acid (25% in water). Both solutions are autoclave-sterilized.

Plasmid Production Method 2—A 30-L seed fermentor was batched with 15 L of medium E (Table 9). The seed reactor was inoculated with 300 mL of frozen inoculum of *E. coli* DH5 strain harboring the V1Jns HIV Flgag plasmid prepared as described in Example 7. The thawing procedure consisted of removing the frozen Nalgene bottle from the freezer and placing it in a stationary 37° C. water bath with periodic vigorous manual shaking. Approximately 20 minutes were required for complete thawing to occur. The bottle was subsequently removed from the water bath and the thawed inoculum was aseptically transferred to an inoculation assembly. The operating conditions were as follows: temperature, 37° C.; airflow, 7.5 L/min; agitation, 250 rpm; and pressure 4.5 PSI. The initial value of the pH was in the 7.0-7.1 range. No pH control was used during the inoculum production. As demand increased, dissolved oxygen level was maintained at a set point greater or equal to 30% throughout the remainder of the fermentation cycle by automatic ramping of the agitation speed within the range of 250-750 rpm.

The cells reached a carbon evolution rate (CER) of 35 mM/L/h in about 7 hours. At that time, a volume of 75 mL of the inoculum fermentor was transferred to a 30-L production fermentor that contained 15 L of medium F (Table 10). The operating conditions were as follows: temperature, 37° C.; airflow, 7.5 L/min; agitation, 250 rpm; and pressure, 4.5 PSI. Dissolved oxygen level was maintained to a set point, greater or equal to 30% of air saturation at ambient pressure, by automatic cascade control of the agitation speed, between 250-700 rpm, and by increase of the airflow and back pressure set points from 7.5 to 12 L/min and from 4.5 to 15 PSI, respectively. These increases were performed at the time of MSG-glycerol feeding. The pH of the culture was maintained within the range of 7.0 to 7.2 by automatic addition of 15% (v/v) phosphoric acid or 30% (v/v) sodium hydroxide throughout the fermentation cycle. Dissolved oxygen level, CER, OUR, and pH of the fermentation broth were all measured on-line.

At about 9.8 hours after inoculation, when on-line measurements for CER read about 35 mMoles/L/h feeding of a solution containing 50% glycerol and 25% monosodium glutamate was automatically initiated at a constant rate of 3.2 g/L/h. To accommodate the high dissolved oxygen demand associated with the higher cell concentration and in order to maintain the DO>30%, the vessel pressure and the airflow were both automatically increased to 15 PSI and 12 L/min respectively (at the time of feeding initiation). Additional control of the DO at greater than 30% was achieved using a computer control loop to the agitator (from 250 rpm to 750 rpm). An amount totaling approximately 2.1 L of feed solution was pumped over 45 hours.

A maximum biomass of 19.9 g/L of dry cell weight was achieved and specific and volumetric plasmid DNA productivities were 29.6 μg plasmid per mg of dry cell weight and 0.588 g/L, respectively. FIG. 10 (panels A and B) presents the CER, growth ($OD_{600}$), and plasmid production profiles.

TABLE 9

Defined Culture Medium E

| Components | Concentrations |
|---|---|
| [1]$KH_2PO_4$ | 7.0 g/L |
| [1]$K_2HPO_4$ | 7.0 g/L |
| [1]$(NH_4)_2SO_4$ | 6.0 g/L |
| [1]Glycerol | 15.0 g/L |
| [1]Ucon | 0.3 mL/L |
| [2]Thiamine Hydrochloride | 0.20 g/L |
| [2]$MgSO_4 \cdot 7H_2O$ | 2.0 g/L |
| [2]Neomycin Sulfate | 0.08 g/L |
| [3]Trace Elements | 1.0 mL/L |

[1]The ingredients were added to 15 L of water, and the fermentor was steam sterilized in place at 123° C. for 25 min.
[2]A concentrated solution (thiamine: 24 g/L; $MgSO_4 \cdot 7H_2O$: 240 g/L; neomycin sulfate: 9.6 g/L) is prepared and filtered sterilized into the seed fermentor to yield the desired final concentrations.
[3]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). The solution is added post sterilization to the fermentor.
The pH of the medium was adjusted to 7.1 prior to inoculation.

TABLE 10

Defined Culture Medium F

| Components | Concentrations |
|---|---|
| [1]$KH_2PO_4$ | 7.0 g/L |
| [1]$K_2HPO_4$ | 7.0 g/L |
| [1]$(NH_4)_2SO_4$ | 6.0 g/L |
| [1]Glycerol | 15.0 g/L |
| [1]Ucon | 0.3 mL/L |
| [2]Thiamine Hydrochloride | 0.60 g/L |
| [2]$MgSO_4 \cdot 7H_2O$ | 2.0 g/L |
| [3]Trace Elements | 1.0 mL/L |

[1]Ingredients are added to 15 L of water, and the fermentor was steam sterilized in place at 123° C. for 25 minutes.
[2]A concentrated solution (thiamine: 72 g/L; $MgSO_4 \cdot 7H_2O$: 240 g/L) is prepared and filtered sterilized into the fermentor to yield the desired final concentrations.
[3]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). The solution is added post sterilization to the fermentor.
The pH of the medium was adjusted to 7.1 prior to inoculation.
Feed solution preparation: A concentrated solution (MSG: 250 g/L; glycerol: 500 g/L) is prepared and autoclaved at 121 C. for 30 minutes.

Plasmid Production Method 3—*E. coli* DH5 strain harboring the V1Jns HIV Flgag plasmid was cultivated in 30 L fermentors containing 15 L of medium G (Table 11). Each production fermentor (30-L) was inoculated with a 300 mL volume of frozen culture prepared as described in Example 7 and thawed as described in Method 2 of this Example. Operating conditions of the fermentors were similar to those described in Method 2 of this Example with the exception that the agitation set point maximum was increased to 800 rpm. The fed-batch process included the initiation of a 60% glycerol feed solution at a constant feed rate when the carbon evolution rate (CER) reached 35 mmol/L/hour. Samples were collected at various time-points following the initiation of the feed solution to monitor plasmid production. The process was terminated 48 hours post inoculation.

A total of 18 production batches were profiled at feed rates ranging from 2.0-12 g/L/h. The effect of each feed rate on plasmid yield was measured by profiling a minimum of two independent batches. Samples were collected throughout the fermentation, and each was assayed twice for plasmid yield in order to examine the standard deviation of the results. Online analyses included OUR/CER monitoring and on-line OD profiling for each batch. FIG. 11 (panel A) shows the results obtained for one batch cultivated at a feed rate of 8.0 g/L/h. Metabolic analysis revealed that although the concentration of thiamine decreases over time, it was not entirely depleted by the end of the fermentation (FIG. 11, panel B). Glycerol was maintained at undetectable levels during the feeding portion of the process and was likely to be the limiting nutrient. The concentration of ammonium remained between 2.5 and 1.5 g/L throughout the cultivation (FIG. 11, panel B). Analyses of the plasmid content show that there is no substantial increase in specific plasmid yield with constant feed rates greater than 8.0 g/L/h (FIG. 12, panel A and B). Maximum plasmid titers of approximately 30-32 μg plasmid/mg DCW specific yield where achieved for feed rates ranging between 8.0-12.0 g/L/h. Dependent on the feeding regimen, volumetric yields ranging from 0.2 g/L to 1.3 g/L were achieved.

TABLE 11

Defined Culture Medium G

| Components | Concentrations |
|---|---|
| [1]$KH_2PO_4$ | 7.0 g/L |
| [1]$K_2HPO_4$ | 7.0 g/L |
| [1]$(NH_4)_2SO_4$ | 6.0 g/L |
| [1]Glycerol | 15.0 g/L |
| [1]Ucon | 1.0 mL/L |
| [2]Thiamine Hydrochloride | 0.60 g/L |
| [2]$MgSO_4 \cdot 7H_2O$ | 2.0 g/L |
| [3]Trace Elements | 1.0 mL/L |

[1]The ingredients were added to 15 L of water and the fermentor was steam sterilized in place at 123° C. for 25 min.
[2]A concentrated solution (thiamine: 72 g/L; $MgSO_4 \cdot 7H_2O$: 240 g/L) is prepared and filtered sterilized into the seed fermentor to yield the desired final concentrations.
[3]Trace Elements are dissolved in 1.2N HCl as a stock solution. Composition: $FeCl_3 \cdot 6H_2O$ (27 g/L), $ZnCl_2$ (2 g/L), $CoCl_2 \cdot 6H_2O$ (2 g/L), $Na_2MoO_4 \cdot 2H_2O$ (2 g/L), $CaCl_2 \cdot 2H_2O$ (1 g/L), $CuCl_2 2H_2O$ (1.27 g/L), and $H_3BO_3$ (0.5 g/L). The solution is added post sterilization to the fermentor. Feed solution preparation. A concentrated solution of glycerol (600 g/L) is prepared and autoclaved at 121° C. for 60 min. The pH of the medium was adjusted prior inoculation to 7.1. The pH was controlled with a 50% ammonium hydroxide solution.

What is claimed is:

1. A process for production of plasmid DNA comprising:
   (a) selecting a highly productive clonal subtype of a strain of *E. coli* transformed with a DNA plasmid comprising:
      (i) observing a phenotypic heterogeneity in a population of colonies generated by the transformed *E. coli*, and selecting as potentially highly productive clonal subtypes those colonies that represent a minor component of said phenotypic heterogeneity in said population of colonies;
      (ii) purifying said potentially highly productive clonal subtypes and determining the productivity of said purified, potentially highly productive clonal subtypes by measuring the plasmid copy number per cell; and,
      (iii) selecting as a highly productive clonal subtype a potentially highly productive clonal subtype that exhibits a higher plasmid copy number per cell in comparison to non-selected, transformed *E. coli* clonal subtypes of the same strain; and,
   (b) cultivating said highly productive clonal subtype with fed-batch fermentation in chemically-defined medium in a fermentation volume of greater than 1000 L, wherein said phenotypic heterogeneity is observed after the transformed *E. coli* is grown on blood agar at about 30° C., and
wherein the potentially highly productive clonal subtypes that represent the minor component of said phenotypic heterogeneity are gray colored-colonies while the major component of said phenotypic heterogeneity are white-colored colonies.

2. The process of claim 1, wherein the potentially highly productive clonal subtypes are purified from the blood agar.

3. The process of claim 2, wherein the plasmid copy number per cell of the purified, potentially highly productive clonal subtypes is determined after cultivating said clonal subtypes in a shake flask with feeding fermentation system using chemically defined medium.

4. The process of claim 3, wherein said strain of *E. coli* is DH5.

5. The process of claim 4, wherein said chemically-defined medium comprises a medium selected from the group consisting of Medium C, Medium D, Medium E, Medium F and Medium G.

6. The process of claim 1, wherein the process further comprises
   (a) duplicate plating the transformed *E. coli* on blood agar and an agar that does not contain blood products;
   (b) growing the *E. coli* at about 30° C. until distinct colonies are visible;
   (c) observing the gray colonies as the minor component of said phenotypic heterogeneity on the blood agar;
   (d) determining which colonies on the agar that does not contain blood products correspond to the gray colonies on the blood agar; and
   (e) purifying said colonies from the agar that does not contain blood products that correspond to the gray colonies on the blood agar,
wherein said purified colonies are the potentially highly productive clonal subtypes.

7. The process of claim 6, wherein the plasmid copy number per cell of the purified, potentially highly productive clonal subtypes is determined after cultivating said clonal subtypes in a shake flask with feeding fermentation system using chemically defined medium.

8. The process of claim 7, wherein said strain of *E. coli* is DH5.

9. The process of claim 8, wherein said chemically-defined medium comprises a medium selected from the group consisting of Medium C, Medium D, Medium E, Medium F and Medium G.

10. The process of claim 6, wherein the agar that does not contain blood products is a chemically-defined agar medium.

11. A process for production of plasmid DNA comprising:
   (a) selecting a highly productive clonal subtype of a strain of *E. coli* transformed with a DNA plasmid comprising:
      (i) observing a phenotypic heterogeneity in a population of colonies generated by the transformed *E. coli* when incubated on blood agar at 30° C. consisting of a minor component of gray-colored colonies and a major component of white-colored colonies, and selecting as potentially highly productive clonal subtypes the gray-colored colonies;
      (ii) purifying said potentially highly productive clonal subtypes, and determining the productivity of said purified, potentially highly productive clonal subtypes by measuring the plasmid copy number per cell; and,
      (iii) selecting as a highly productive clonal subtype a potentially highly productive clonal subtype that exhibits a higher plasmid copy number per cell in comparison to non-selected, transformed *E. coli* clonal subtypes of the same strain; and, (b) cultivating said highly productive clonal subtype with fed-batch fermentation in chemically-defined medium.

12. The process of claim 11, wherein said strain of *E. coli* is DH5.

13. The process of claim 11, wherein said chemically-defined medium comprises a medium selected from the group consisting of Medium C, Medium D, Medium E, Medium F and Medium G.

* * * * *